US012329822B2

(12) United States Patent
Jordan et al.

(10) Patent No.: US 12,329,822 B2
(45) Date of Patent: Jun. 17, 2025

(54) ANTIMICROBIAL TAILORED CHITOSAN

(71) Applicant: UNIVERSITÉ DE GENÈVE, Geneva (CH)

(72) Inventors: Olivier Jordan, Prangins (CH); Viorica Patrulea, Le Grand-Saconnex (CH); Gerrit Borchard, Arzier (CH); Bee Ha Gan, La Chaux-de-Fonds (CH); Jean-Louis Reymond, Bulle (CH)

(73) Assignee: UNIVERSITÉ DE GENVE, Geneva (CH)

( * ) Notice: Subject to any disclaimer, the term of this patent is extended or adjusted under 35 U.S.C. 154(b) by 770 days.

(21) Appl. No.: 17/608,595

(22) PCT Filed: May 5, 2020

(86) PCT No.: PCT/EP2020/062433
§ 371 (c)(1),
(2) Date: Nov. 3, 2021

(87) PCT Pub. No.: WO2020/225255
PCT Pub. Date: Nov. 12, 2020

(65) Prior Publication Data
US 2022/0193244 A1 Jun. 23, 2022

(30) Foreign Application Priority Data

May 6, 2019 (EP) .................................... 19172726

(51) Int. Cl.
| | | |
|---|---|---|
| A61K 47/00 | (2006.01) | |
| A61K 47/61 | (2017.01) | |
| A61K 47/69 | (2017.01) | |
| A61P 31/04 | (2006.01) | |

(52) U.S. Cl.
CPC .......... *A61K 47/61* (2017.08); *A61K 47/6903* (2017.08); *A61P 31/04* (2018.01)

(58) Field of Classification Search
CPC .... A61K 47/61; A61K 47/6903; A61K 38/04; A61P 31/04; A61L 26/0066
See application file for complete search history.

(56) References Cited

U.S. PATENT DOCUMENTS

2007/0292387 A1* 12/2007 Jon ...................... A61K 9/0048
514/10.9

OTHER PUBLICATIONS

International Search Report from corresponding PCT Application No. PCT/EP2020/062433 dated Jul. 16, 2020.
Written Opinion from corresponding PCT Application No. PCT/EP2020/062433 dated Jul. 16, 2020.
Patrulea, V., et al., "Peptide-decorated chitosan derivatives enhance fibroblast adhesion and proliferation in wound healing," Carbohydrate Polymers, 142: 114/123 (2016).
Patrulea, V., et al., "Chitosan as a starting material for wound healing applications," European Journal of Pharmaceutics and Biopharmaceutics, 97: 417-426 (2015).
Patrulea, V., et al., "Nanocomplexes based on chitosan-peptide derivatives towards wound healing promotion," New Biotechnology, 44 (2018), 1 page.
Barbosa, M., et al., "Tethering antimicrobial peptides onto chitosan: Optimization of azide-alkyne "click" reaction conditions," Carbohydrate Polymers, 165: 384-393 (2017).
Sahariah, P., et al., "Antimicrobial peptide shows enhanced activity and reduced toxicity upon grafting to chitosan polymers," Chemical Communications, 51(58): 11611-11614 (2015).
Muszanska, A.K., et al., "Antiadhesive Polymer Brush Coating Functionalized with Antimicrobial and RGD Peptides to Reduce Biofilm Formation and Enhance Tissue Integration," Biomacromolecules, 15(6): 2019-2026 (2014).

* cited by examiner

*Primary Examiner* — Jeanette M Lieb
(74) *Attorney, Agent, or Firm* — Harness Dickey & Pierce P.L.C.

(57) ABSTRACT

The invention relates to a bio-conjugate comprising a chitosan derivative coupled to an antimicrobial peptide (AMP) for use in the treatment or prevention of a microbial infection, for example in wound healing. The invention also provides a nanoparticle formulation or a gel/hydrogel formulation or a lyophilized foam formulation comprising the bio-conjugate of the invention.

19 Claims, 8 Drawing Sheets

Specification includes a Sequence Listing.

FIG: 1
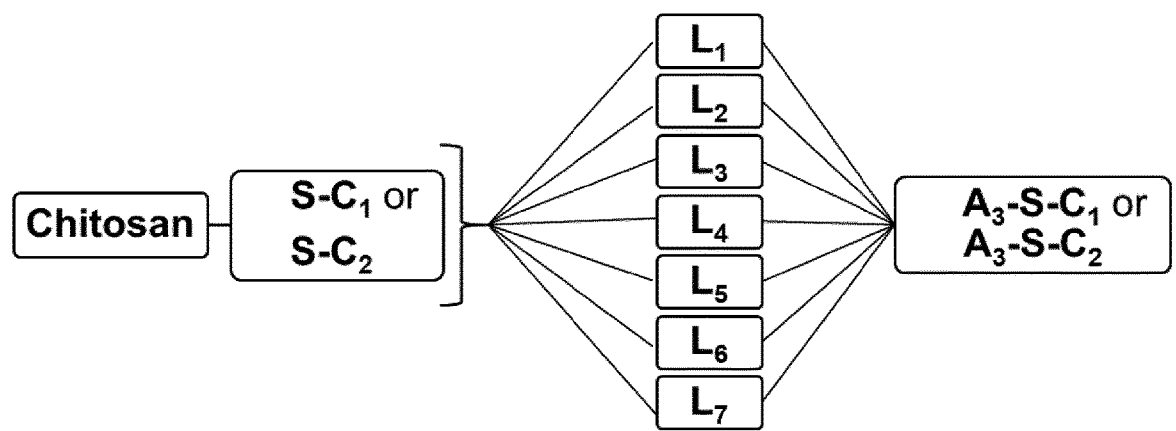
FIG: 2
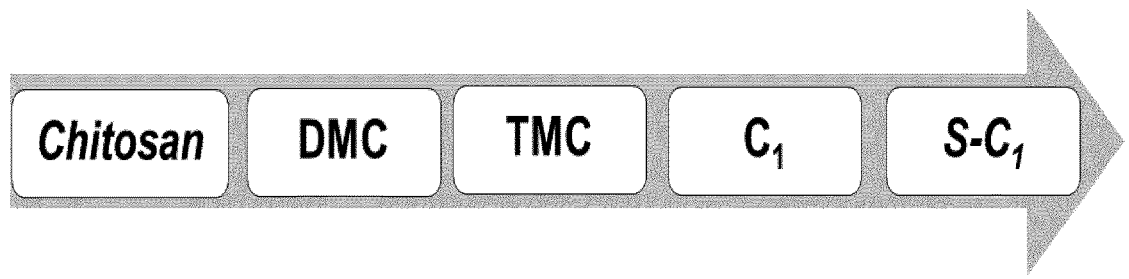

FIG: 3
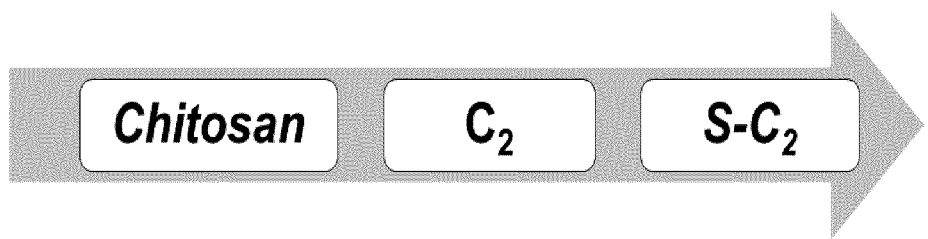
FIG: 4
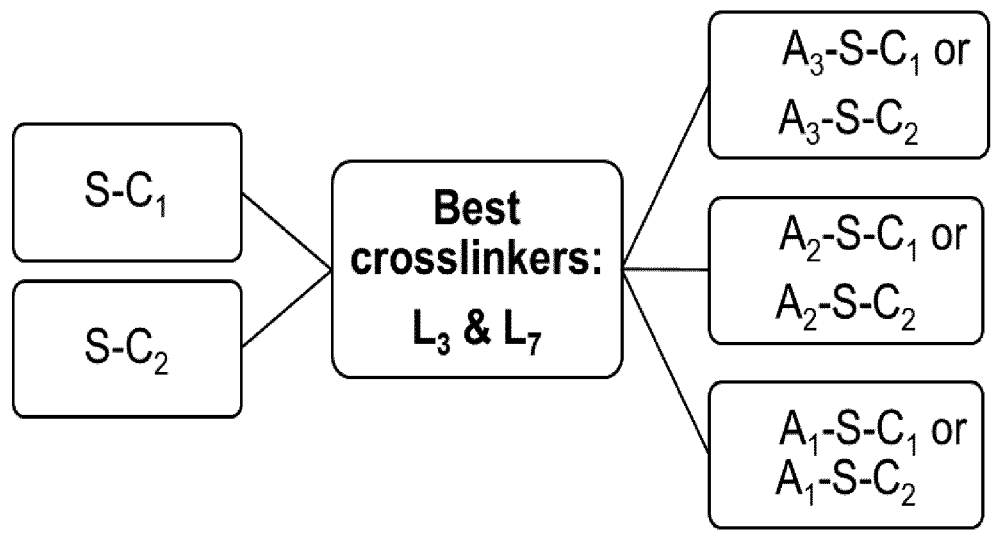

FIG: 5
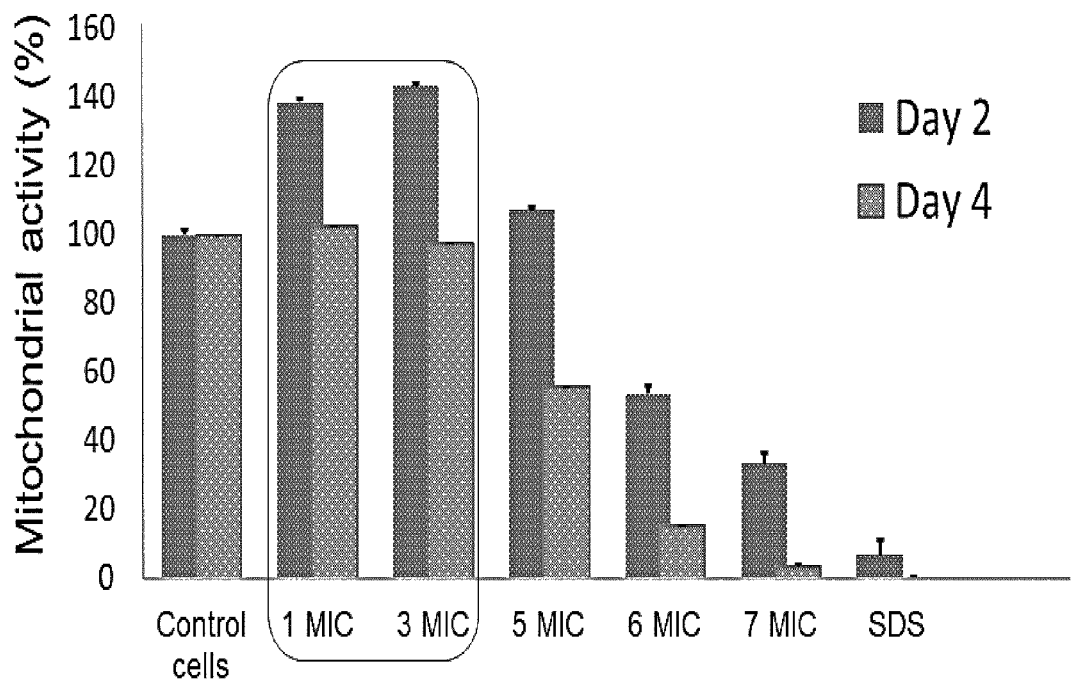
FIG: 6
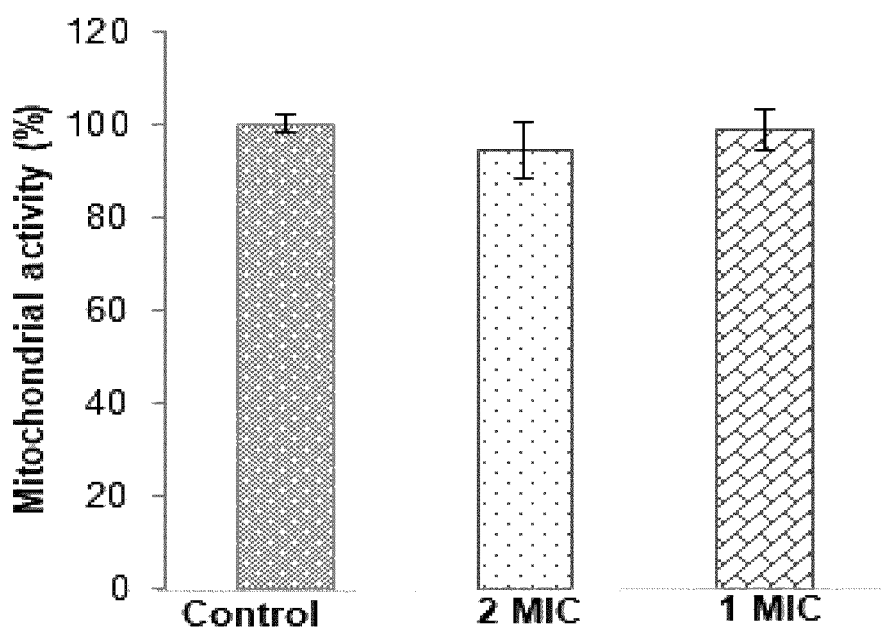

FIG: 7
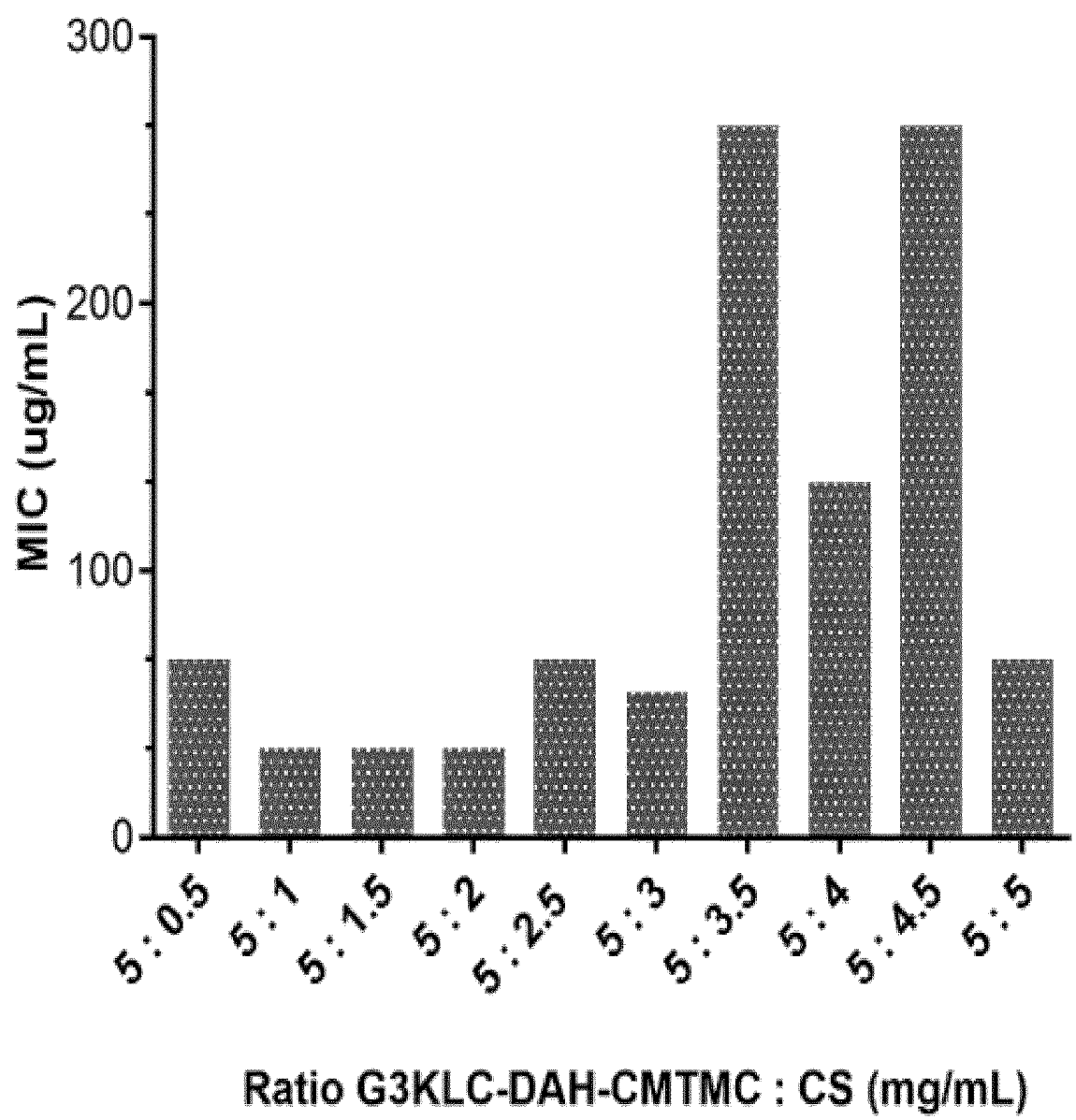

FIG: 8
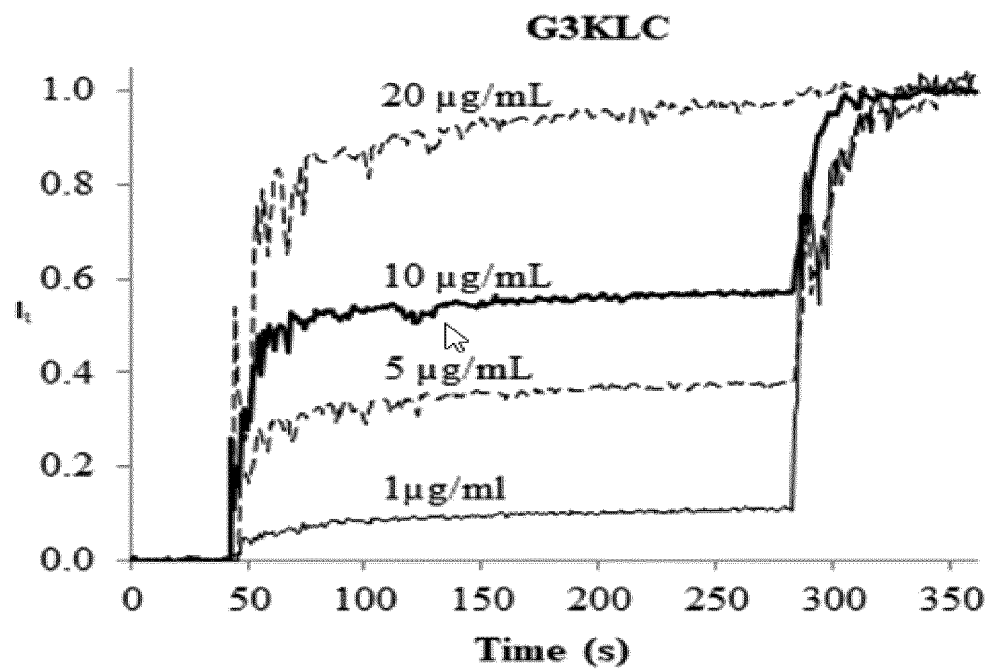
8A
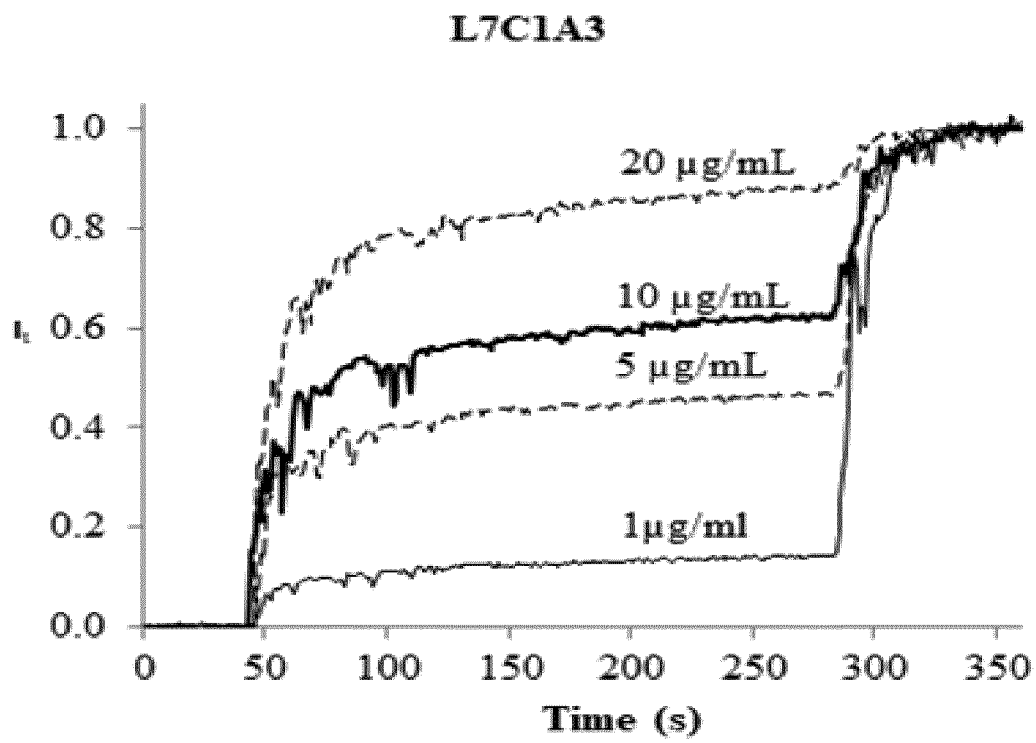
8B

FIG: 9
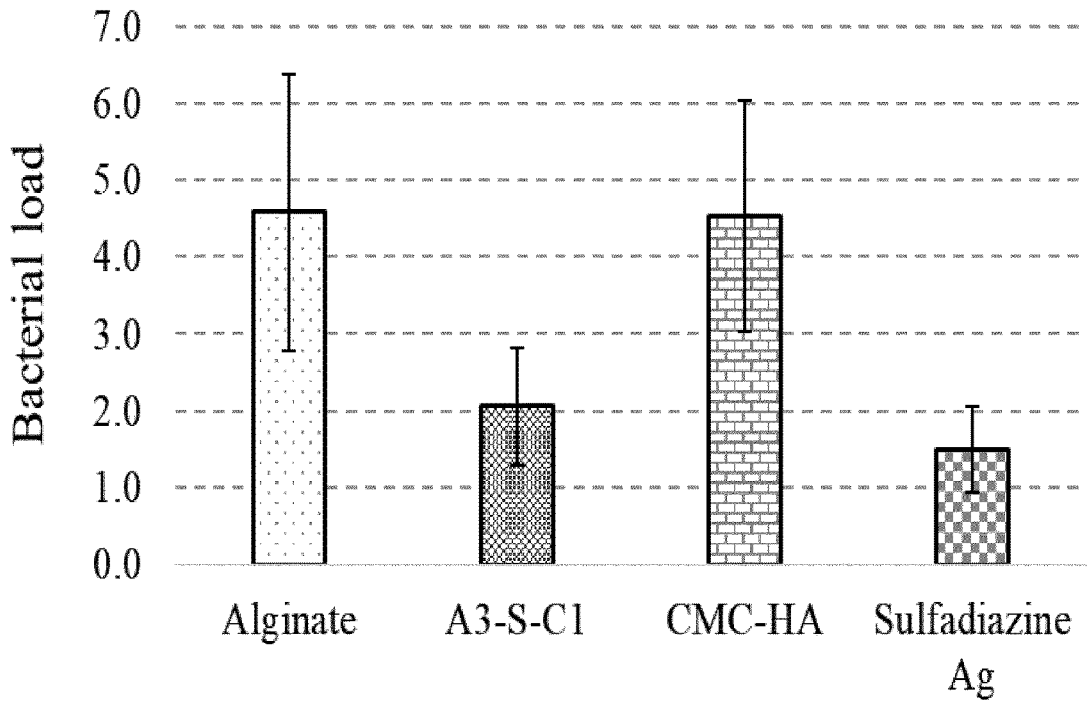
FIG. 10
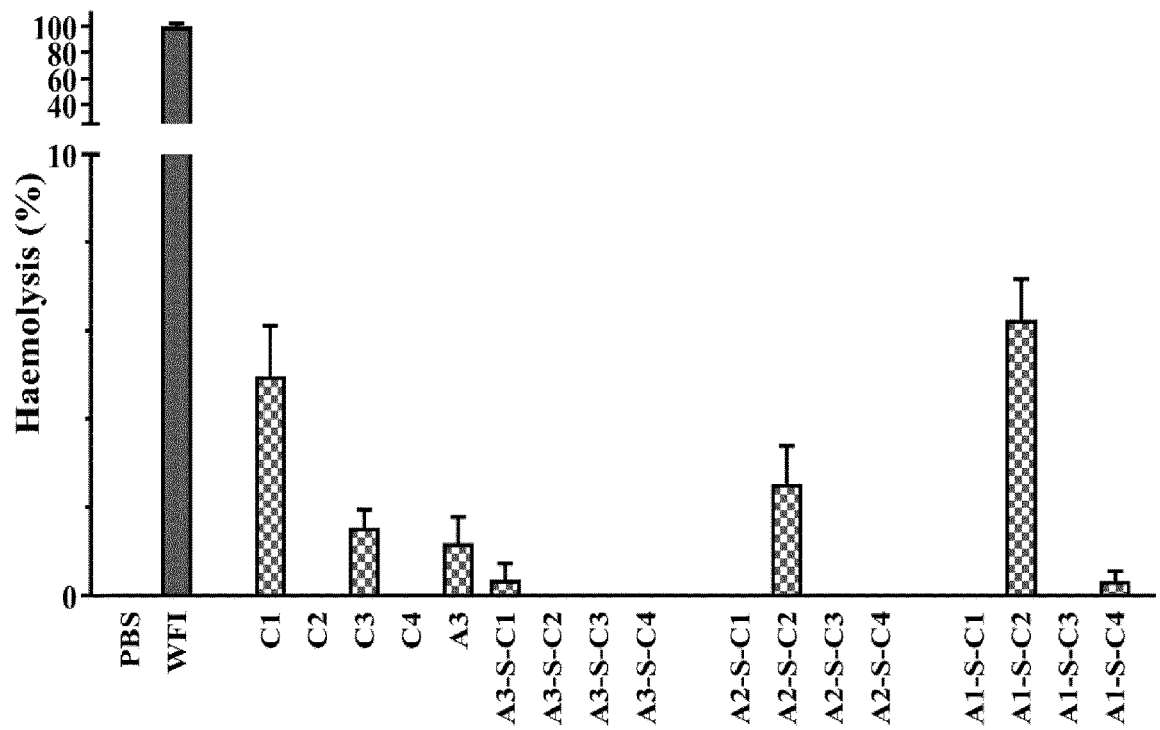

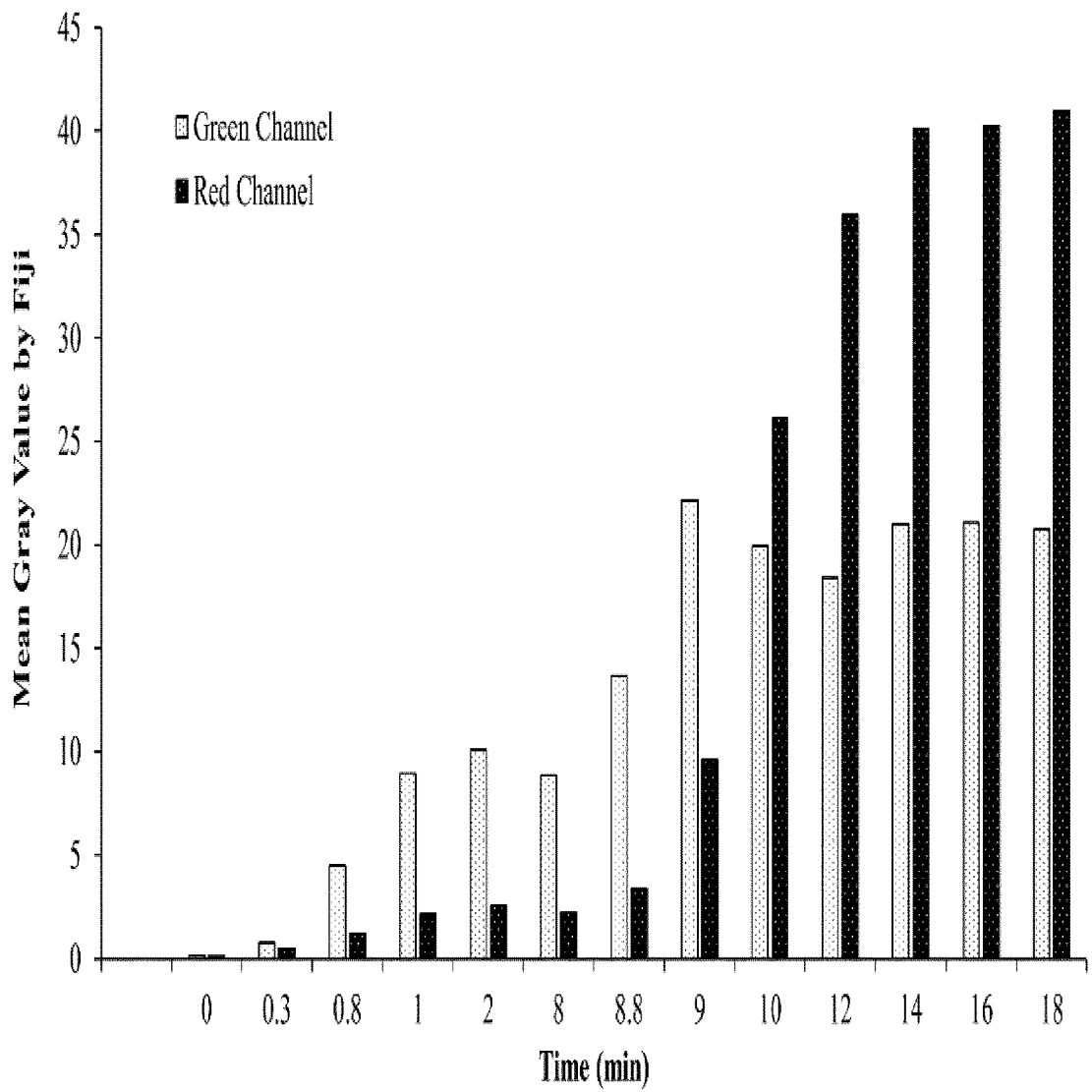
FIG: 11

FIG: 12
| Control *P. aeruginosa* | AMPD G3KL (40 µg/mL) | $A_3$-S-$C_1$ (40 µg/mL) |
|---|---|---|
| 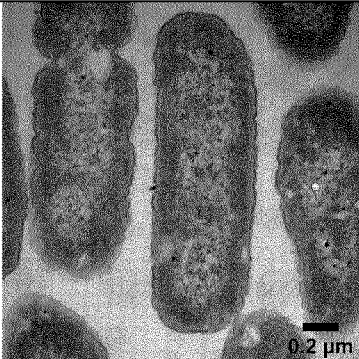 | 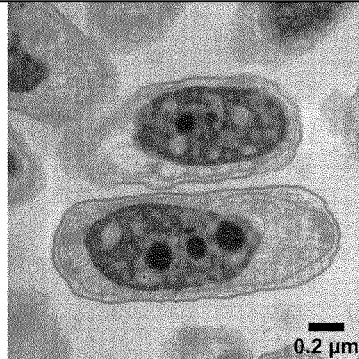 | 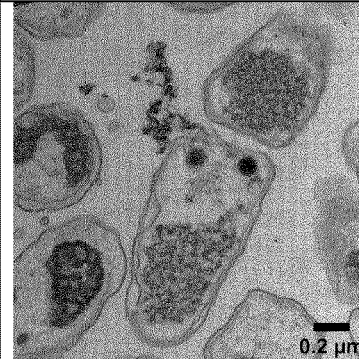 |
| $A_3$-S-$C_2$ (40 µg/mL) | $A_3$-S-$C_3$ (40 µg/mL) | $A_3$-S-$C_4$ (40 µg/mL) |
| 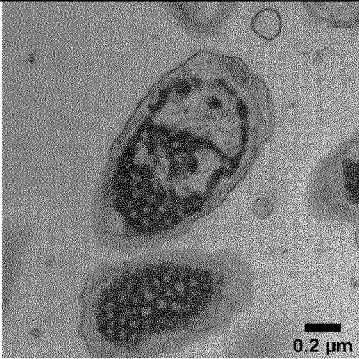 | 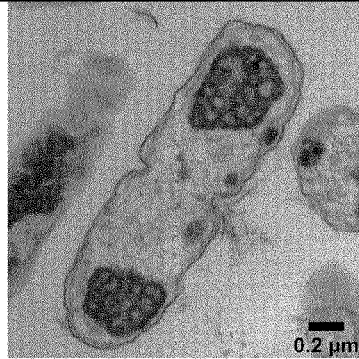 | 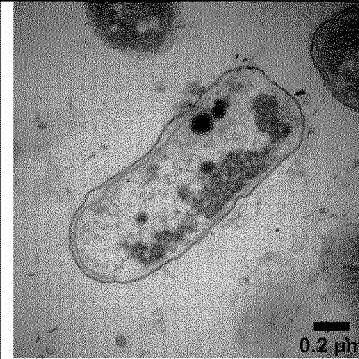 |
| G3KLK(fluo)C-CMTMC (40 µg/mL) | | |
| 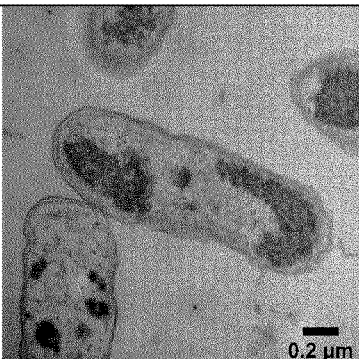 | | |

ANTIMICROBIAL TAILORED CHITOSAN

CROSS-REFERENCE TO RELATED APPLICATIONS

This patent application is a U.S. National Phase Application of International Patent Application No. PCT/EP2020/062433 filed on 5 May 2020, which claims priority to European Patent Application No. 19172726.2 filed on 6 May 2019.

REFERENCE TO A SEQUENCE LISTING

The present disclosure contains references to nucleic acid or amino acid sequences which have been submitted concurrently herewith as the sequence listing text file entitled "6170-000138-US-NP_Revised_11_Dec_2024_ST25.TXT," file size 5,200 Bytes (B), created on 11 Dec. 2024. The aforementioned sequence listing is hereby incorporated by reference in its entirety pursuant to 37 C.F.R. § 1.52(e)(5).

FIELD OF THE INVENTION

The invention relates to a bio-conjugate comprising a chitosan derivative coupled to antimicrobial peptides (AMPs) for use in the treatment or prevention of microbial infections such as wound healing. The invention also provides a nanoparticles formulation or a gel/hydrogel formulation or a lyophilized foam formulation comprising the bio-conjugate of the invention.

BACKGROUND OF THE INVENTION

Antimicrobial resistance to many antibiotics is a global healthcare issue that continues to worsen despite the efforts in finding solutions. One of the three most problematic bacteria is *Pseudomonas aeruginosa*, which has been reported as the most challenging gram-negative bacteria in chronic wounds. In clinics, already existing conventional bandages are no longer effective against multidrug-resistant (MDR) bacteria that show increasing resistance to conventional drugs [1].

Several peptides, known as antimicrobial peptides (AMP), have been found to have antimicrobial activity, but they are quickly degraded once in contact with human serum and therefore, lose their activity. Moreover, most of them are toxic and have a short half-life [2]. Another promising approach is the use of antimicrobial peptide dendrimers (AMPDs), which showed better activity than conventional AMPs, but still with a quite high toxicity and poor stability in human serum of only 9 hours [3]. Therefore, there is an urgent need to develop new strategies to deliver these AMPs and AMPDs avoiding their degradation, still keeping a low toxicity at therapeutic concentration.

A strategy to deliver AMPs is to use a vehicle such as nanoparticles (NPs), lipid self-assemblies or hydrogels to potentially improve half-life upon nanoparticle incorporation. However, maintaining activity is not ensured and transport is hindered by particle diffusion.

Another strategy is to couple the active peptide to a carrying biopolymer, such as a polysaccharide. However, attempts to date have led to limited efficacy or safety.

In previous work, the inventors designed a chitosan conjugated to a cell-adhesion peptide, RGD (V. Patrulea et al. "Peptide-decorated chitosan derivatives enhance fibroblast adhesion and proliferation in wound healing" Carbohydrate Polymers. 2016, vol. 142, p. 114-123). In this study, RGDC (SEQ ID NO: 18) peptide was grafted onto the chitosan derivative 1,6-diaminohexane-O-carboxymethyl-N,N,N-trimethyl chitosan (DAH-CMTMC). Peptide grafting was achieved through sulfhydryl groups using sulfosuccinimidyl (4-iodoacetyl)amino-benzoate (sulfo-SIAB crosslinker). Bio-adhesion and proliferation assays confirmed that coatings of RGDC (SEQ ID NO: 18)-functionalized chitosan derivatives enhanced fibroblast proliferation and adhesion, a prerequisite for optimal wound healing. However, no enhancement of RGD activity or synergy with the polymer activity was observed. RGDC (SEQ ID NO: 18) was coupled to CMTMC to enhance fibroblast cell adhesion and migration, two important factors for wound regeneration. RGD has no antibacterial activity and was specifically used as a chemoattractant to guide fibroblast migration. RGDC (SEQ ID NO: 18) covalent immobilization is a strategy to enhance the rate of fibroblasts adhesion and proliferation rate on chitosan derivative surfaces. The immobilized RGDC (SEQ ID NO: 18) peptide on chitosan derivatives proved to be successful in promoting fibroblast adhesion and accelerating cell proliferation.

In Patrulea et al. 2015: "Chitosan as a starting material for wound healing applications" European Journal of Pharmaceutics and Biopharmaceutics, 97:417-426, doi.org/10.1016/j.ejpb.2015.08.004, it was shown that RGD immobilization on chitosan derivatives and their incorporation into 3-D scaffolds leads to an enhanced cell adhesion and biocompatibility. GRGDS (SEQ ID NO: 19) peptide was used to induce cell adhesion and migration. Nanoparticles functionalized with the peptide were able, in vitro, to promote fibroblast adhesion and spreading of human dermal fibroblasts at a 3-fold increased area compared to an inactive scrambled peptide. In addition, this document presented some examples of chitosan derivatives used to accelerate wound healing and introduced some strategies for using them in different formulations: sponges, nanoparticles, scaffolds, gels, dressings or films. Formulations such as nanoparticles, gels and hydrogels based on RGD-CMTMC to induce cell adhesion and migration were discussed.

In Patrulea et al. 2018: "Nanocomplexes based on chitosan-peptide derivatives towards wound healing promotion", New Biotechnology 44:S14, doi.org/10.1016/j.nbt.2018.05.166, it was disclosed formulations based on the chitosan derivative O-carboxymethyl-N,N,N-trimethyl-chitosan (CMTMC) grafted with RGDC (SEQ ID NO: 18) peptide. Besides, hydrogels were obtained by mixing RGDC (SEQ ID NO: 18)-functionalized chitosan with hyaluronic acid (HA) at a 1:1 volume ratio. Human dermal fibroblasts treated with formulations based on RGDC (SEQ ID NO: 18)-derivatized chitosan showed a spread phenotype and increased motility compared to CMTMC, indeed they have the potential to accelerate cell migration in vitro and promote healing of chronic wounds. Formulations such as nanoparticles, gels and hydrogels based on RGDC (SEQ ID NO: 18)-CMTMC to induce cell adhesion and migration were also prepared.

Barbosa et al. 2017: "Tethering antimicrobial peptides onto chitosan: Optimization of azide-alkyne "click" reaction conditions", Carbohydrate Polymers, 165(1):384-393, discloses immobilization of AMP onto biomaterials as an emergent field of research, towards the creation of novel antimicrobial materials able to avoid formation of biofilms on the surfaces of medical devices. The chemical route towards one such material is reported, where chitosan was used as biocompatible carrier for the covalent grafting of Dhvar-5, a well-known potent AMP, via the chemoselective ("click") Cu(I)-catalyzed azide-alkyne cycloaddition (CuAAC). This document does not provide any proof or data of AMP-chitosan bioactivity, no Minimal Inhibitory Concentration (MIC) on any microbial strain is shown, and conjugate solubility at neutral pH is not described. No experimental proof of the efficacy of this conjugate is provided, neither in term of the stability of the AMP-chitosan system over more than few days.

Sahariah et al. 2015: "Antimicrobial peptide shows enhanced activity and reduced toxicity upon grafting to chitosan polymers" Chemical Communications 51(58) 11611-11614, doi.org/10.1039/C5CC04010H, discloses that Anoplin-chitosan conjugates were synthesized by copper-catalyzed alkyne-azide coupling (CuAAC) reaction of multiple peptides through 2-azidoacetyl groups on chitosan. Initial findings show activity against several microbial strain, but fails to show any synergistic effect of the conjugate with respect to chitosan and AMP alone. Activity on the long term (e.g. 1 week) is also not shown. In terms of toxicity, only 50% hemolysis rate are shown, failing to prove low hemolytic activity.

Agnieszka et al. 2014: "Antiadhesive Polymer Brush Coating Functionalized with Antimicrobial and RGD Peptides to Reduce Biofilm Formation and Enhance Tissue Integration" Biomacromolecules 15(6): 2019-2026, doi.org/10.1021/bm500168s, discloses that anti-adhesive polymer brushes composed of block copolymer Pluronic F-127 (PF127) were functionalized with antimicrobial peptides (AMP), able to kill bacteria on contact, and arginine-glycine-aspartate (RGD) peptides to promote the adhesion and spreading of host tissue cells. The antiadhesive and antibacterial properties of the coating were investigated with three bacterial strains: *S. aureus, S. epidermidis*, and *P. aeruginosa*. This document reports that RGDs attached to the extended end of a polymer chain are expected to increase tissue cell adhesion. Additionally, it has been shown that polymers functionalized with RGD peptides possess antiadhesive properties against certain bacterial strains, but unfortunately, other pathogens adhere preferentially to cell adhesion moieties like RGD peptides. A combination of AMPs and RGDs incorporated in a polymer brush coating may yield a trifunctional surface with antiadhesive, bactericidal, and tissue-integrating properties. Indeed, this document deals with the anti-adhesion properties of RGD for certain bacterial strains, but this is not about inhibiting bacterial growth or bactericidal activity of RGD moiety. To conclude, this document discloses combined use of anti-adhesive PF127 molecules to repel adhering bacteria, a PF127-AMP conjugates to kill bacteria on contact and PF127-RGD conjugates to enhance tissue integration. RGD is not intended for antimicrobial activity and no RGD antimicrobial activity is demonstrated.

Building on this knowledge, the purpose of the present invention is to provide an efficient peptidic conjugate based on chitosan that meets the requirement of potent antimicrobial activity, preserved and long lasting activity in biological environment and low toxicity against healthy tissues.

BRIEF DESCRIPTION OF THE INVENTION

One of the objects of the present invention is to provide a long last active bio-conjugate comprising a chitosan derivative coupled to antimicrobial peptides (AMPs) according to the general formula (I):

$$C-S-L-Cys-AMP \qquad (I)$$

where:
C represents a chitosan derivative selected from the group consisting of O-carboxymethyl chitosan (CMC), O-carboxymethyl-N,N,N-trimethyl chitosan (TMC), N-(4-N,N-dimethylamino cinnamyl) chitosan (DMCMC) or methylated N-(4-pyridylmethyl) chitosan chloride (MPyMeC);
S is a spacer consisting of a $C_1$-$C_{12}$ aliphatic carbon chain terminated with one amino group at both ends;
L is a sulfo-crosslinker selected from the group consisting of: 4-(N-maleimidomethyl)cyclohexane-1-carboxylic acid 3-sulfo-N-hydroxysuccinimide (sulfo-SMCC); sulfosuccinimidyl 4-(N-maleimidophenyl)butyrate (sulfo-SMPB); sulfo-N-succinimidyl 4-maleimidobutyrate (sulfo-GMBS); N-(ε-maleimidocaproyloxy) sulfosuccinimide (sulfo-EMCS); N-(κ-maleimidoundecanoyloxy) sulfosuccinimide (sulfo-KMUS); sulfosuccinimidyl 6-[3'-(2-pyridyldithio)propionamido] hexanoate (sulfo-LC-SPDP) and sulfosuccinimidyl (4-iodoacetyl)aminobenzoate (sulfo-SIAB);
Cys is cysteine;
and AMP is a peptide or a peptide dendrimer with an antimicrobial activity represented by a minimum inhibitory concentration MIC lower than 100 μg/mL, with the proviso that said peptide or peptide dendrimer is not RGD peptide; and wherein said long lasting active bio-conjugate preserves its antimicrobial activity for at least 1 week when applied to a patient, for use in the treatment or prevention of microbial infections.

Another object of the invention is to provide a nanoparticles formulation or a gel/hydrogel formulation or a lyophilized foam formulation comprising the bio-conjugate of the invention.

In particular, the bio-conjugate according to the invention is suitable for the treatment or prevention of microbial infectious comprises bacterial infection diseases, local bacterial infections, infected wounds, abscess, soft tissue infections, diabetic infections, diabetic foot ulcer infections (DFU), antimicrobial treatment of patient tissues, osteomyelitis, treatment of burn infections, post-surgical wound infections, biomaterial-associated infections such as endotracheal tubes, artificial heart valves, urinary catheters, central venous catheters, prostheses, orthopaedic devices, contact lenses, dentures, prosthetic joints and other implant surface-associated infections.

Other objects and advantages of the invention will become apparent to those skilled in the art from a review of the ensuing detailed description, which proceeds with reference to the following illustrative drawings, and the attendant claims.

BRIEF DESCRIPTION OF THE FIGURES

FIG. 1: shows the schematic representation of $G_3KL$-Cys coupling to chitosan backbone through different sulfo-crosslinkers before choosing the best crosslinker. Single letter code: [L] for crosslinkers; [S] for spacer; [C] for chitosan derivative and [A] for AMPD-Cys. More detailed, $L_1$=sulfo-SMCC; $L_2$=sulfo-SMPB; $L_3$=sulfo-GMBS; $L_4$=sulfo-EMCS; $L_5$=sulfo-KMUS; $L_6$=sulfo-LC-SPDP; $L_7$=sulfo-SIAB; $C_1$=CMTMC; $C_2$=CMC and A3=$G_3KL$-Cys AMPD-Cys.

FIG. 2: illustrates the Pathway of S—$C_1$ synthesis.

FIG. 3: shows the S—$C_2$ synthesis.

FIG. 4: illustrates the coupling of two different generations of AMPDs ($G_3KL$, $G_2KL$) and one AMP (RH9L) conjugated with cysteine through selected sulfo-crosslinkers as sulfo-SIAB and sulfo-EMCS to DAH-CMC or DAH- CMTMC. Single letter code: [L] for crosslinkers; [C] for chitosan derivative and [A] for AMPD-Cys. Specifically, $L_3$=sulfo-GMBS; $L_7$=sulfo-SIAB; $C_1$=CMTMC; $C_2$=CMC; $A_3$=$G_3$KL-Cys AMPD; $A_2$=$G_2$KL-Cys AMPD and $A_1$=RH9L-Cys AMP.

FIG. 5: shows the mitochondrial activity of HDF (human dermal fibroblasts) treated with $G_3$KL-Cys-DAH-CMTMC at different MICs over 2 and 4 days (1×MIC=16 µg/mL; 3×MIC=64 µg/mL; 5×MIC=256 µg/mL; 6×MIC=512 µg/mL; 7×MIC=1024 µg/mL).

FIG. 6: is a WST-1 assay on NPs (ratio 5:5) with 1 and 2×MIC against fibroblast cells as control (1×MIC=1024 µg/mL of polymer, which is equivalent to 277 µg/mL of $G_3$KL-Cys and 2×MIC=2048 µg/mL of polymer corresponding to 554 µg/mL of $G_3$KL-Cys.

FIG. 7: shows MIC values for NPs formed at different ratios between A3-S—C1 and CS. Single letter code: [C] for chitosan derivative; [S] for DAH spacer and [A] for AMPD-Cys. Specifically, S=1,6-diaminohexane; $C_1$=CMTMC; $C_2$=CMC; $A_3$=$G_3$KL-Cys AMPD; $A_2$=$G_2$KL-Cys AMPD and $A_1$=RH9L-Cys AMP.

FIG. 8: presents fluorescein leakage assay from phosphatidyl glycerol lipid vesicles for different concentration of $G_3$KL-Cys dendrimer peptide (A) or $L_7C1A_3$ linear peptide (B). Thin solid line: 1 µg/mL; thin dashed line: 5 µg/mL; thick solid line: 10 µg/mL; thick dashed line: 20 µg/mL.

FIG. 9: illustrates *P. aeruginosa* growth in mice wound one day after inoculation.

FIG. 10: represents the hemolysis results for all conjugates. Single letter code: [C] for chitosan derivative; [S] for DAH spacer and [A] for AMPD-Cys. More detailed, $C_1$=CMTMC; $C_2$=CMC; $C_3$=CMPyMeC; $C_4$=CMDMCMC; $L_7$=sulfo-SIAB; $A_3$=$G_3$KL-Cys; $A_2$=$G_2$KL-Cys and A1=RH9L-Cys AMPD.

FIG. 11: represents the uptake of the fluorescently labeled Fluo-$A_3$-S—$C_1$ (Green channel: chitosan conjugate uptake) and subsequent rapid bacterial death (red channel: propidium iodide uptake).

FIG. 12: shows the mechanism of action of chitosan-conjugates coupled to $G_3$KLC AMPD ($A_3$) assessed by TEM on *P. aeruginosa*. Single letter code: [C] for chitosan derivative; [S] for DAH spacer and [A] for AMPD-Cys. More detailed, $C_1$=CMTMC; $C_2$=CMC; $C_3$=CMPyMeC; $C_4$=CMDMCMC; A3=$G_3$KL-Cys; A2=$G_2$KL-Cys and $A_1$=RH9L-Cys AMPD.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and new-born subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

As used herein, the term "prevent" refers to the prophylactic treatment of a subject who is at risk of developing a condition (e.g., microbial (e.g., bacterial) infection) resulting in a decrease in the probability that the subject will develop the condition.

A "carrier" or a "pharmaceutical acceptable carrier" refers to, for example, a diluent, adjuvant, preservative (e.g., Thimersol, benzyl alcohol), anti-oxidant (e.g., ascorbic acid, sodium metabisulfite), solubilizer (e.g., Tween™ 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3<rd>Ed.), American Pharmaceutical Association, Washington, 1999.

"Linker" refers to a chemical moiety comprising a covalent bond or a chain of atoms that covalently attach at least two compounds. The linker can be linked to any synthetically feasible position of the compounds, but preferably in such a manner as to avoid blocking the compounds desired activity. Linkers are generally known in the art.

The term "antimicrobials" as used herein indicates a substance that kills or inhibits the growth of microorganisms or microbes such as bacteria, fungi, viruses, or protozoans, particularly bacteria.

"Antimicrobial peptides" (AMPs), also called host defense peptides (HDPs) are part of the innate immune response found among all classes of life. Fundamental differences exist between prokaryotic and eukaryotic cells that may represent targets for antimicrobial peptides. These peptides are potent, broad spectrum antibiotics which demonstrate potential as novel therapeutic agents. Antimicrobial peptides have been demonstrated to kill Gram negative and Gram positive bacteria, enveloped viruses, fungi and even transformed or cancerous cells. Unlike the majority of conventional antibiotics it appears that antimicrobial peptides frequently destabilize biological membranes, can form transmembrane channels, and may also have the ability to enhance immunity by functioning as immunomodulators. Antimicrobial activity is commonly defined by a minimum inhibitory concentration MIC lower than 100 µg/mL.

The tripeptide Arg-Gly-Asp (RGD) consists of Arginine, Glycine, and Aspartate. It was originally identified as the amino acid sequence within the extracellular matrix protein fibronectin that mediates cell attachment. The RGD cell binding sequence has since been identified in other extracellular matrix proteins, including vitronectin and laminin. The family of membrane proteins known as integrins act as receptors for these cell adhesion molecules via the RGD motif. RGD has never been reported for having antibacterial activity or biofilm inhibition property.

For example Agnieszka et al. 2014, uses RGD and only shows its use for adhesive properties useful in tissue regeneration. No antibacterial activity is shown. This is widely disclosed in the literature since RGD peptide acts as a biological cue which, once properly displayed by an adequate carrier, should guide the fibroblasts for enhanced adhesion, migration and proliferation (E. Ruoslahti 1996 "RGD and other recognition sequences for integrins" Annu. Rev. Cell Dev. Biol., 12, pp. 697-715, doi.org/10.1146/annurev.cellbio.12.1.697; Tarone et al. 2000 "Integrin function and regulation in development" Int. J. Dev. Biol., 44: 725-731).

In Agnieszka et al. 2014, FIGS. 2 and 3 displaying antimicrobial activity have been obtained without using any RGD. On the contrary, authors hope that RGD will not interfere negatively with antimicrobial activity "one may expect that the presence of RGD will not influence the antimicrobial properties of the coating".

A "spacer" is a carbon aliphatic chain having a length of up to 12 carbons, whose purpose is to provide flexibility and freedom of orientation of the further attached peptide.

"Ratio" in the synthesis of the chitosan derivatives refers to the molar ratio of the saccharide units of the chitosan derivative to the AMP or AMPD molecules.

It is usually accepted that "synergy" occurs when the combined action of two or more agents is greater than the sum of their individual effects. In other words, synergy is said to occur when the combined action of two or more agents is greater than could have been predicted based on the performance of the agents when used alone.

Knowing that the AMPs are already effective on their own, Applicants developed a technological platform intended to protect the active peptide from its environment by grafting it to a linear, biodegradable and biocompatible polymer such as chitosan. Applicants found that grafting AMPs-Cys (including AMPDs-Cys) of different sizes to chitosan derivatives through an aliphatic spacer and sulfo-crosslinkers could improve the antimicrobial activity and the lifetime of the peptides.

By "sulfo-crosslinker", it is meant heterobifunctional, water-soluble amine-to-sulfhydryl crosslinkers with N-hydroxysuccinimide esters and maleimide or haloacetyl reactive groups or pyridyldithiol reactive groups. Eventually they can comprise an alkyl chain of $C_1$ to $C_{12}$ length, preferably $C_1$ to $C_{10}$ (between 7.3 to 16.3 Å).

Applicants selected 7 sulfo-crosslinkers to achieve the grafting: 4-(N-maleimidomethyl)cyclohexane-1-carboxylic acid 3-sulfo-N-hydroxysuccinimide ester (sulfo-SMCC); sulfosuccinimidyl 4-(N-maleimidophenyl)butyrate (sulfo-SMPB); sulfo-N-succinimidyl 4-maleimidobutyrate (sulfo-GMBS); N-(ε-maleimidocaproyloxy) sulfosuccinimide ester (sulfo-EMCS); N-(κ-maleimidoundecanoyloxy) sulfosuccinimide ester (sulfo-KMUS); sulfosuccinimidyl 6-[3'-(2-pyridyldithio)propionamido]hexanoate (sulfo-LC-SPDP) and sulfosuccinimidyl (4-iodoacetyl)aminobenzoate (sulfo-SIAB).

In addition, several sulfo-crosslinker may be used for the purpose of the invention, which are but not limited to: m-Malemidobenzoyl-N-hydroxysulfosuccinimide ester (sulfo-MBS) or sulfo-LC-SMPT 4-Sulfosuccinimidyl 6[-α-methyl-cc-(2-pyridyldithio)toluamido]hexanoate.

However, there are other similar crosslinkers with the same functional groups, but they are missing sulfo-groups and are water-insoluble, therefore resulting in insoluble products, which might be used as well for different applications.

Such examples are: succinimidyl (4-iodoacetyl)aminobenzoate (SIAB); succinimidyl 4-(N-maleimidomethyl)cyclohexane-1-carboxylate (SMCC); succinimidyl 4-(N-maleimidomethyl)cyclohexane-1-carboxy-(6-amidocaproate) (LC-SMCC); succinimidyl 4-(p-maleimidophenyl)butyrate (SMPB); N-succinimidyl 3-(2-pyridyldithio)propionate (SPDP); succinimidyl 6-(3(2-pyridyldithio)propionamido) hexanoate (LC-SPDP); N-succinimidyl S-acetylthioacetate (SATA), N-ε-malemidocaproyl-oxysuccinimide ester (EMCS) and N-γ-maleimidobutyryl-oxysuccinimide ester (GMBS).

In addition, several non-sulfo-crosslinkers may be used for the purpose of the invention, which are—but not limited to: 4-succinimidyloxycarbonyl-alpha-methyl-alpha(2-pyridyldithio)toluene (SMPT); N-[α-Maleimidoacetoxy] succinimide ester (AMAS); N-[β-Maleimidopropyloxy]succinimide ester (BMPS); N-[γ-Maleirnidobutyryloxy] succinimide ester (GMBS); Succinimidyl-6-[β-maleimidopropionamido]hexanoate (SMPH); m-Malemidobenzoyl-N-hydroxysuccinimide ester (MBS); N-Succinimidyl iodoacetate (SIA); succinimidyl 3-[bromoacetamido] propionate (SBAP); PEGylated N-succinimidyl S-acetylthioacetate (SAT(PEG)4); PEGylated SMCC (SM(PEG)$_x$) or PEGylated SPDP (PEG$_x$-SPDP).

This is an important breakthrough, as these antimicrobial peptides are considered very effective in fighting against MDR bacteria [3]. Herein, Applicants analyzed the in vitro activity, such as minimal inhibitory concentration (MIC), of AMPDs-chitosan molecules on *P. aeruginosa*. Moreover, Applicants could couple to the chemical platform not only high molecular weight AMPDs like $G_3KL$ (4.6 kDa), but also smaller AMPDs like $G_2KL$ (2.2 kDa) and linear AMPs like RH9L (1.6 kDa).

The antimicrobial activity of the peptide, once coupled to the chitosan derivative, may lead to several results as follows: either (i) a decreased effect, e.g., due do chitosan steric hindrance—leading to an antagonist effect, or (ii) an additive effect, combining chitosan and peptide antimicrobial effect without interactions between both, or (iii) a synergistic effect, whereby the antimicrobial effect of the compound of the invention is increased. While coupling to large biopolymers may be expected to hinder the activity of the peptide, the inventors demonstrated that, surprisingly, the chitosan-AMPDs-Cys of the invention shown strong synergy when compared to the activities of the chitosan and AMPD alone (see results in Example 1).

Without being bound by theory, the above-mentioned synergistic effect might be partially attributed to a sustained antimicrobial activity of the chitosan-AMP-Cys. This is attributed to enhanced proteolytic stability of the chitosan-AMP-Cys construct. More specifically, the short half-life of the antimicrobial peptide might be prolonged by the presence of covalently coupled chitosan, acting by steric hindrance to protect the peptide from enzymatic degradation.

One purpose of the invention is to provide materials capable of protecting wounds against infection and, at the same time, promoting wound healing. In this view, angiogenesis would be an important advantage. Angiogenesis is actually expected from the chitosan-AMPD-Cys construct, related to AMPD intrinsic pro-angiogenic properties, combined with tissue regenerative properties of chitosan. As a result, potential promotion of cell migration (e.g., fibroblast or keratinocytes involved wound healing) can be obtained. AMPDs, more specifically $G_3KL$, promoted angiogenesis in a human umbilical vein endothelial cells (HUVEC) and chorioallantoic membrane (CAM) model, which is an important factor for accelerating wound healing (Abdel-Sayed, et al. 2016: "Anti-Microbial Dendrimers against Multidrug-Resistant *P. aeruginosa* Enhance the Angiogenic Effect of Biological Burn-wound Bandages" Scientific Reports 6(1), 22020. doi.org/10.1038/srep22020.). Therefore, one could expect that chitosan-AMPD-Cys conjugates besides preserving the antimicrobial activity, will keep the angiogenic effect as well upon coupling.

Lower toxicity towards HDF (human dermal fibroblasts) is another potential advantage of coupling covalently the AMP-Cys or AMPD-Cys to the chitosan derivative. In addition, the hemolytic potential of the chitosan-AMPD-Cys construct may be lowered upon grafting to chitosan, compared to the original peptide. Such reduced hemolysis would be an important asset to enable the delivery of higher antimicrobial peptide doses to the patient.

Noteworthy, the covalent coupling strategy did preserve the helical structure of the peptide as shown in Example 2. Moreover, similar mechanism of action was demonstrated for the peptide alone and the chitosan-couple peptide, specifically the killing of the bacteria via both internal and external membrane disruption, as shown by vesicle leakage data of Example 2.

One particular purpose of this technology is to develop efficient "weapons" for topical application in case of chronic wounds, such as burns, diabetic and non-healing wounds that favor the formation of a biofilm on top of the wound. Therefore, polyelectrolyte formulations such as nanoparticles, hydrogels and foam-like bandages can be developed for accommodation and protection of the AMPDs within these nanostructures and later released at needed time.

Nanoparticles can be prepared for example by using a "one-shot" method by mixing positively charged AMPD-chitosan to a negatively charged polymer such as chondroitin sulfate (CS).

Hydrogels and foams, blends of chitosan and another biopolymer such as hyaluronic acid can be used as a filling matrix, as it gives minimal adverse reactions. Addition of the "active principle" (i.e. the derivatized AMPD-chitosan or AMP-chitosan) to the matrix provides antibacterial activity. Thus, the protected AMPDs or AMPs embedded in the formulation is efficiently delivered with a preserved, sustained release, durable efficacy against bacteria or other microbes.

One object of the invention is to provide a long lasting active bio-conjugate comprising a chitosan derivative coupled to antimicrobial peptides (AMPs) according to the general formula (I):

C—S-L-Cys-AMP  (I)

where:
- C represents a chitosan derivative selected from the group consisting of O-carboxymethyl chitosan (CMC), O-carboxymethyl-N,N,N-trimethyl chitosan (TMC), N-(4-N,N-dimethylamino cinnamyl) chitosan (DMCMC) or methylated N-(4-pyridylmethyl) chitosan chloride (MPyMeC);
- S is a spacer consisting of a $C_1$-$C_2$ aliphatic carbon chain terminated with one amino group at both ends;
- L is a sulfo-crosslinker selected from the group consisting of 4-(N-maleimidomethyl)cyclohexane-1-carboxylic acid 3-sulfo-N-hydroxysuccinimide (sulfo-SMCC); sulfosuccinimidyl 4-(N-maleimidophenyl)butyrate (sulfo-SMPB); sulfo-N-succinimidyl 4-maleimidobutyrate (sulfo-GMBS); N-(ε-maleimidocaproyloxy) sulfosuccinimide (sulfo-EMCS); N-(κ-maleimidoundecanoyloxy) sulfosuccinimide (sulfo-KMUS); sulfosuccinimidyl 6-[3'-(2-pyridyldithio)propionamido] hexanoate (sulfo-LC-SPDP) and sulfosuccinimidyl (4-iodoacetyl)aminobenzoate (sulfo-SIAB);
- Cys is cysteine;
- and AMP is a peptide or a peptide dendrimer with an antimicrobial activity represented by a minimum inhibitory concentration MIC lower than 100 µg/mL, with the proviso that said peptide or peptide dendrimer is not RGD peptide;
- and wherein said long lasting active bio-conjugate preserves its antimicrobial activity for at least 1 week when applied to a patient, for use in the treatment or prevention of microbial infections.

A surprising technical effect is observed, as a synergy between chitosan and AMP in terms of antimicrobial activity, as shown in the examples.

In addition it is also demonstrated that, besides synergistic potentiation of the AMP activity, this particular conjugation with chitosan derivatives according to the invention preserve the antimicrobial activity on the long term. In particular antimicrobial activity is preserved for at least one week, for more than two weeks, preferably three weeks, more preferably one month, even more preferably 2 months, preferably for more than 3 months, for more than 4 months and even for more than 5 months and even more preferably for 6 months or more.

This property represents an important asset to ensure a sustained antimicrobial action when applied to a patient's wound. Usually activity of non-conjugated AMPs in patient's wound is limited to few hours. For instance, LL-37 displays strong antimicrobial activity against both Gram positive (*S. aureus* (MIC: 14 µg/mL); *S. mutans* (MIC: 28 µg/mL)) and Gram negative bacteria (*H. pylori* (MIC: 14 µg/mL); *N. meningitides* (MIC: 28 µg/mL)) (Leszczynska et al. 2013 "Antibacterial activity of the human host defence peptide LL-37 and selected synthetic cationic lipids against bacteria associated with oral and upper respiratory tract infections" J Antimicrob Chemother 68(3): 610-618 (doi: 10.1093/jac/dks434)), but fast degradation (less than 6 h) in the presence of proteases (Gronberg et al. 2011 "Stability of the cathelicidin peptide LL-37 in a non-healing wound environment" Acta Derm Venereol 91(5):511-515. (doi: 10.2340/00015555-1102)). IDR-1018 acts as well against both Gram positive (*S. aureus* (MIC: 5 µg/ml) and Gram negative bacteria (*P. aeruginosa* (MIC: 19 µg/ml)) and *M. tuberculosis* (MIC: 16 µg/mL) (Rivas-Santiago et al. 2013 "Ability of Innate Defence Regulator Peptides IDR-1002, IDR-HH2 and IDR-1018 to Protect against *Mycobacterium tuberculosis* Infections in Animal Models" PLoS One 8(3): e59119; doi: 10.1371/journal.pone.0059119), though is stable for only a few hours (Chen et al. 2018 "Inhibition and Eradication of *Pseudomonas aeruginosa* Biofilms by Host Defence Peptides" Sci Rep 8, 10446; doi.org/10.1038/s41598-018-28842-8).

As further shown in the examples, the particular conjugation of AMPs to the chitosan derivatives further preserves the killing mechanism of the parent peptide, inducing a rapid permeabilization of bacterial membrane death. This is clearly excluding any "osmotic" mechanism.

Antibacterial and antimicrobial activities are conventionally described by the MIC, minimal inhibitory concentration, this excludes antibacterial activity due to osmotic pressure. Applicants have shown that AMPD-coupled to chitosan derivatives are able to disrupt inner and outer membrane of the *P. aeruginosa*.

"Minimum inhibitory concentrations (MICs) are defined as the lowest concentration of an anti-microbial that will inhibit the visible growth of a microorganism after overnight incubation" (J. M. Andrews 2001 "Determination of minimum inhibitory concentrations", Journal of Antimicrobial Chemotherapy, 48(1):5-16, doi.org/10.1093/jac/48.suppl_1.5). Common measure of antimicrobial activity is obtained through minimal inhibitory concentration. The community considers generally useful MIC to be lower than 100 µg/mL of the agent.

According to the invention, AMP is a peptide or a peptide dendrimer with an antimicrobial activity represented by a minimum inhibitory concentration MIC lower than 100 µg/mL. Preferably, the minimum inhibitory concentration MIC is lower than 80 µg/mL, more preferably lower than 50 µg/mL and even more preferably lower than 30 sg/mL.

Table 1 presents the activity of some AMPs with their antimicrobial activity against different microbial strains.

TABLE 1

Biological activity of some AMPs against different bacterial strains.

| AMP | MIC (µg/mL) | Bacterial strain |
|---|---|---|
| RH9L | 16 | *P. aeruginosa* |
| OP-145 | 6.1-9.2 | *E. coli* |
|  | 9.2-18.3 | *P. aeruginosa* |
|  | 18.3 | *C. albicans* |
| LL-37 | 14 | *S. aureus* |
|  | 28 | *S. mutans* |
|  | 14 | *H. pylori* |
|  | 28 | *N. meningitides* |
| IDR-1018 | 5 | *S. aureus* |
|  | 19 | *P. aeruginosa* |

No MIC has been reported for RGD due to the absence of activity. On the contrary, inhibition has been reported, for instance for AMPs rich in histidine which show fungicide activity, while when in the presence of RGD, this activity is abolished (Wu et al. 2014 "Novel Anticandidal Activity of a Recombinant *Lampetra japonica* RGD3 Protein" I. Microbiol. Biotechnol. 24(7), 905-913; dx.doi.org/10.4014/jmb.1312.12037).

Preferably, the antimicrobial peptide AMP is either a glycosylated or non-glycosylated linear peptide, or dendrimer peptide.

According to one embodiment of the invention, the linear peptide is selected from the group consisting of LinKL7, AG30, AG30/5C, AH90, CW49, Cys-KR12, hBD-1, His1, hL1-11, IDR-1018, KYKKALKKLAKLL (SEQ ID NO: 14), LL-37, Novexatin®, Omiganan, OP-145, Pexiganan®, RH9L, Temporin A and B or a combination thereof wherein:

(SEQ ID NO: 1)
AG30 is MLSLIFLHRLKSMRKRLDRKLRLWHRKNYP;

(SEQ ID NO: 2)
AG30/5C is MLKLIFLHRLKRMRKRLKRKLRLWHRKRYK;

(SEQ ID NO: 3)
AH90 is ATAWDFGPHGLLPIRPIRIRPLCG;

(SEQ ID NO: 4)
CW49 is APFRMGICTTN;

(SEQ ID NO: 5)
Cys-KR12 is CKRIVQRIKDFLR;

(SEQ ID NO: 6)
hBD-1 is DHYNCVSSGGQCLYSACPIFTKIQGTCYRGKAKCCK;

(SEQ ID NO: 7)
His1 is DSHEKRHHGYRRKFHEKHHSH REFPFYGDYG SNYLYDN;

(SEQ ID NO: 8)
hL1-11 is GRRRRSVQWCA;

(SEQ ID NO: 9)
IDR-1018 is VRLIVAVRIWRR;

(SEQ ID NO: 10)
LL-37 is LLGDFFRKSKEKIGKEFKRIVQRIKDFLRNLVPRTES;

(SEQ ID NO: 11)
Novexatin ® is (cyclo)-RRRRRRR-(cyclo);

(SEQ ID NO: 12)
OP-145 is IGKEFKRIVERIKRFLRELVRPLR;

(SEQ ID NO: 13)
Pexiganan ® is GIGKFLKKAKKFGKAFVKILKK;

(SEQ ID NO: 14)
RH9L is KYKKALKKLAKLL;

(SEQ ID NO: 15)
Temporin A is FLPLIGRVLSGIL;

(SEQ ID NO: 16)
Temporin B is LLPIVGNLLKSLL;
and (SEQ ID NO: 17)
LinKL7 is KLKLKLKLKLKLKL.

According to another embodiment of the invention, the dendrimer peptide (AMPD) is selected from the group consisting of $G_1KL$, $G_2KL$, TNS18, $G_3KL$, $G_3RL$, $G_3KK_1$, $G_3KK_2$, $G_3LL_1$, $G_3LL_2$, $G_3KF$, $G_3KW$, $DG_3kl$, T4, T5, T7, T10, T13, T23, T25, T31, T32, T35, T36 or a combination thereof wherein:

$G_1$ stands for first-generation peptide dendrimers:

Where $G_1KL$ is $(KL)_2KKL$;

$G_2$ stands for second-generation peptide dendrimers:

Where $G_2KL$ is $(KL)_4(KKL)_2KKL$;

TNS18 is a second-generation peptide dendrimer consisting of 19 amino acids with the presence of a lipid: $(OF)_4(KBL)_2KKLK(C_{10})$ $G_3$ stands for third-generation peptide dendrimer:
Where
$G_3KL$ is $(KL)_8(KKL)_4(KKL)_2KKL$,
$G_3RL$ is $(RL)_8(KRL)_4(KRL)_2KRL$,
$bG_3RL$ is $(RL)_8(BRL)_4(BRL)_2BRL$,
$G_3KK_1$ is $(KK)_8(KLK)_4(KLK)_2KLK$,
$G_3KK_2$ is $(KK)_8(KLL)_4(KKK)_2KLL$,
$G_3LL_1$ is $(LL)_8(KLL)_4(KKK)_2KKK$,
$G_3LL_2$ is $(LL)_8(KKK)_4(KLL)_2KKK$,
$G_3KF$ is $(KF)_8(KKF)_4(KKF)_2KKF$,
$G_3KW$ is $(KW)_8(KKW)_4(KKW)_2KKW$,
$G_3KY$ is $(KY)_8(KKY)_4(KKY)_2KKY$,
$G_3KA$ is $(KA)_8(KKA)_4(KKA)_2KKA$,
$G_3LA$ is $(LA)_8(KLK)_4(KLA)_2KKL$,
$DG_3kl$ is $(kl)_8(kkl)_4(kkl)_2kkl$;
And where:
T4: $(KL)_8(KK)_4(KLKL)_2KLKL$,
T5: $(KL)_8(KKL)_4(KLL)_2KKL$,
T7: $(KL)_8(KKL)_4(KKLL)_2KKKL$,
T10: $(KL)_8(KK)_4(KLKL)_2KKLL$,
T13: $(KL)_8(KK)_4(KLLK)_2KLLK$,
T23: $(KL)_8(KKL)_4(KLL)_2KKKK$,
T25: $(KL)_8(KKL)_4(KLL)_2KKLL$,
T28: $(KL)_8(KKL)_4(KLK)_2KLLL$,
T31: $(KL)_8(KKL)_4(KKLL)_2KKKK$,
T32: $(KL)_8(KKL)_4(KKLL)_2KLKK$,
T35: $(KL)_8(KKL)_4(KLKL)_2KKKL$,
T36: $(KL)_8(KKL)_4(KLKL)_2KLKK$.

The skilled in the art would clearly understand that one-letter code stands for amino acids (upper case: L-, lower case: D-amino acids):

A: alanine; B: 2,3-diaminopropanoic acid; C: cysteine; D: aspartic acid; F: phenylalanine; H: histidine; I: isoleucine; K: branched lysine; L: leucine; M: methionine; N: asparagine; O: ornithine; P: proline; Q: glutamine; R: arginine; S: serine; T: threonine; V: valine; W: tryptophan; Y: tyrosine.

Advantageously, the bio-conjugate of the invention can be used for the treatment or prevention of microbial infection selected from the list consisting of bacterial, fungal, yeast and/or viral infection.

In accordance with an embodiment of the invention, the bacterial infection comprises a gram positive or gram-negative infection.

In particular, the bacterial or yeast infection is a *Pseudomonas aeruginosa, Escherichia coli, S. aureus, S. epidermis, Klebsiellae pneumoniae, Acinetobacter baumannii, B. subtilis, E. aerogenes, C. freundii, Staphylococcus* spp, *Streptococcus* spp, *Enterococcus* spp, *Proteus* spp, *Candida* spp, *Apophysomyces* spp, *Aspergillus, Mucor* spp., *Porphymonas gingivalis, Prevotella intermedia, Treponema denticola, Tannerella forsynthesis* or *Aggregatibacter actinomycetemcomitans* infections.

Preferably, the sulfo-crosslinker of the bio-conjugate according to the invention is selected among the group consisting of sulfo-N-succinimidyl 4-maleimidobutyrate (sulfo-GMBS) and sulfosuccinimidyl (4-iodoacetyl)aminobenzoate (sulfo-SIAB).

More preferably, the spacer S of the bio-conjugate according to the invention is 1,12-diamino-alkane, or 1,6-diaminohexane (DAH).

In a particular embodiment of the invention, the molar ratio between the chitosan derivative and the antimicrobial peptides (AMPs-Cys) is 1-10/1-10, preferably 2/1 or preferably 5/1.

Ideally, the bio-conjugate of the invention can be used in the treatment or prevention of microbial infectious comprises bacterial infection diseases, local bacterial infections, infected wounds, abscess, soft tissue infections, diabetic infections, diabetic foot ulcer infections (DFU), antimicrobial treatment of patient tissues, osteomyelitis, periodontal diseases, treatment of burn infections, post-surgical wound infections, biomaterial-associated infections such as endotracheal tubes, artificial heart valves, urinary catheters, central venous catheters, prostheses, orthopaedic devices, contact lenses, dentures, prosthetic joints and other implant surface-associated infections.

In accordance with one aspect of the instant invention, medical devices or implants comprising at least one bio-conjugate of the invention are provided, along with methods of making the same. As used herein, the term "medical device" or "medical implant" includes devices, implants, and materials that are permanently implanted and those that are temporarily or transiently present in the patient. In a particular embodiment, at least part of the exposed surface of the medical device or implant is coated with at least one bio-conjugate of the instant invention. In a particular embodiment, the medical device or implant comprises a plastic (e.g., polyethylene terephthalate) or a metal (e.g., titanium). In a particular embodiment, the bio-conjugate of the invention is covalently attached to the surface of the medical implant or device. In another particular embodiment, the bio-conjugate is coated on the implant surface taking advantage of the film-forming ability of chitosan.

Another object of the invention is to provide nanoparticles formulation comprising the bio-conjugate of the invention as identified above.

A further object of the invention is to provide a gel/hydrogel formulation or a lyophilized foam formulation comprising the bio-conjugate as identified above.

Preferably, the gel/hydrogel or lyophilized foam formulation is adapted for topical application.

A yet further object of the invention is to provide a pharmaceutical composition comprising the bio-conjugate of the invention and a pharmaceutical acceptable carrier, wherein said pharmaceutical composition is formulated for medical or veterinary use.

The composition of the instant invention can be administered to an animal, in particular a mammal, more particularly a human, in order to treat, inhibit, and/or prevent a microbial (e.g., bacterial such as by *E. coli*, MRSA, etc.) infection (e.g., the composition may be administered before, during, and/or after a microbial infection). The composition of the instant invention may also comprise at least one other antimicrobial agent (e.g., an antibiotic). The additional antimicrobial agent may also be administered in a separate composition from the antimicrobial peptides of the instant invention. The composition may be administered at the same time and/or at different times (e.g., sequentially). The composition(s) comprising at least one antimicrobial peptide of the instant invention and the composition(s) comprising at least one additional antibiotic may be contained within a kit.

As used herein, the term "antibiotic" refers to antimicrobial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

Pharmaceutical composition containing the bio-conjugate of the invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, topical, intracranial, and intravitreal.

Antimicrobial resistance is a global healthcare concern that continues to worsen despite the efforts in finding solutions. Therefore, new efficient "weapons" to kill bacteria are needed.

Several peptides, known as antimicrobial peptides (AMPs), hold great potential against microbial infections. However, their clinical application is hindered by different challenges, including toxicity, low selectivity, fast degradation and short half-life. Covalent coupling of AMPs to chitosan showed to preserve biological activity of the AMPs against *P. aeruginosa*, one of the most challenging multidrug resistant bacteria in chronic wounds, such as burns, diabetic and non-healing wounds that favor the formation of a biofilm on top of the wound.

In particular, AMPs/AMPDs-Cys were covalently coupled to chitosan through a controlled chemistry (see the examples). Conventional techniques for covalent coupling through 1-ethyl-3-(3-dimethyl-aminopropyl)-carbodiimide (EDC) and N-hydroxysuccinimide (NHS) result in low peptide grafting in a uncontrolled manner, substituting either carboxyl groups on position 3 or 6, or none, or both chitosan carboxymethyl moieties. Thus, Applicants have developed a new technology for peptide grafting having the advantage of controlling the degree of substitution. This organic solvent-free reaction uses water-soluble reagents for improved degree of grafting.

Surprisingly, the degree of conjugation of AMP-Cys to chitosan was determined to be as high as 30% for all the conjugates using amino acid analysis. The results showed that covalent grafting of AMP-Cys or AMPD-Cys to chitosan preserved the activity of the peptides and efficiently killed *P. aeruginosa* at a MIC (minimal inhibitory concentration) of 3-16 pg/mL (see the examples).

For topical application, nanoparticles (NPs) suspensions were obtained by ionic gelation of polyelectrolytes. NPs were characterized for their size and charge. Stability was demonstrated in different media.

Thus, covalent grafting of AMPs-Cys to chitosan overcomes the drawbacks and limitations of the AMPs alone. Nanoparticles can be developed for accommodation and further protection of the AMPs within these nanostructures and later efficiently released at needed time against bacteria.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

Example 1: Polymer Synthesis and Characterization of its Antimicrobial Activity

AMPs/AMPDs Coupling to Chitosan Derivatives

AMPs/AMPDs grafting to the chitosan backbone is shortly illustrated in FIG. 1. It starts from chitosan to 1,6-diamino-hexane-O-carboxymethyl-N,N,N,-trimethyl-chitosan (DAH-CMTMC) (illustrated as S—$C_1$) or to 1,6-diamino-hexane-N,O-carboxymethyl (DAH-CMC) (illustrated as S—$C_2$) to $G_3$KL-Cys-DAH-CMTMC (illustrated as $A_3$-S—$C_1$) or $G_3$KL-Cys-DAH-CMC (illustrated as $A_3$-S—$C_2$) synthesis done using 7 different sulfo-cross-linkers, given in the letter code as L., wherein n is a value from 1 to 7.

DAH-CMTMC Synthesis (S—C1)

DAH-CMTMC was synthesized as previously described [4] with the following steps (FIG. 2):
1) methylation from chitosan primary amine to a tertiary amine leading to N,N-dimethyl-chitosan (DMC);
2) DMC methylation leading to N,N,N-trimethyl-chitosan (TMC);
3) carboxymethylation of available hydroxyl groups from TMC to O,O-carboxymethyl-TMC (CMTMC or illustrated as C1);
4) amination of CMTMC to lead to 1,6-diamino-hexane-CMTMC (DAH-CMTMC, illustrated as S—$C_1$).

Step 1 is important for the protection of chitosan hydroxyl groups, further useful for TMC and CMTMC ($C_1$) synthesis, which allows a controlled peptide grafting. Step 2 is important to confer cationic charges for making nanocomplexes and enhance solubility. Step 3 is to further make possible peptide coupling; Step 4 is the addition of a 6-carbon spacer to improve the accessibility of the peptidic ligand to its target and preserving peptide activity.

DAH-CMC Synthesis (S—C2)

This synthesis starts with chitosan carboxymethylation to spacer addition, illustrated as S—$C_2$ (FIG. 3) and was synthesized with minor modifications as previously described [4].
1) Carboxymethylation of hydroxyl groups from chitosan to O-carboxymethyl-chitosan (CMC). Briefly, chitosan was suspended in isopropanol (1 g chitosan in 100 mL) and left to mix overnight at 45° C. Then, 40% NaOH (0.5 mL) was added during 20 min followed by another 45 min of stirring. Chloroacetate (1.2 g) was added to the reaction mixture over 25 min and left for stirring for another 3 h at 60° C. under nitrogen atmosphere. Cold water was added to quench the reaction, followed by pH adjustment to neutral adding few drops of acetic acid glacial. Filtration and washing with pure methanol was done after precipitation in methanol 70% (v/v). The resulting O-carboxymethyl-chitosan (CMC) was then dried, and dialyzed for 3 days against Milli-Q water. Dialyzed CMC was lyophilized and submitted to further analysis.
2) Amination of CMC to form diaminohexane-CMC (DAH-CMC, illustrated as S—C). Briefly, CMC (500 mg) powder was dissolved in TRIS buffer (1 M; pH 9.0) at high temperature until boiling point. When the reaction solution reached room temperature, carbodiimide reaction was initiated by adding EDC (0.8 M) and sulfo-NHS (0.2 M) and left for stirring for 2 h at room temperature. Subsequently, DAH (1,6-diaminohexane) spacer-arm (0.4 M) was added to the reaction mixture after removing unreacted reagents. Then, the whole reaction was left under stirring for 2 days. The aminated mixture DAH-CMC was purified using dialysis tubes (Amicon® Ultra-15, cut-off 10 kDa) and then washed with Milli-Q water. The final product was lyophilized and the chemical structure analyzed.

AMPs/AMPDs Grafting on Derivatized Chitosan

Coupling all of the AMPs/AMPDs-Cys ($A_1$, $A_2$ and $A_3$) to derivatized chitosan ($C_1$ or $C_2$) was achieved using a modified protocol, as previously reported [4]. First, 10 mg S—$C_1$ or S—$C_2$ polymer was added to 10 mL borate buffer, pH 8.0 containing 0.05 M EDTA was left for stirring and heating until the boiling point. Then, a sulfo-crosslinker ($L_1$ to $L_7$) (1.7 mg/mL dissolved in borate buffer, pH 8.0) was added at a molar ratio of 2:1 to $A_1$, $A_2$ or $A_3$. The reaction was left stirring in the dark for 1 h at 40° C. The unreacted sulfo-crosslinker was washed by dialysis in Amicon tubes (cut-off 12-14 kDa) and centrifugation at 3220×g at 4° C. and later solubilized in 10 mL borate buffer. Afterwards, one of $A_1$, $A_2$ or $A_3$ (at 3 mg/mL in TCEP (Tris(2-carboxyethyl)phosphine)) was added to the reaction mixture at amino groups chitosan saccharide unit/AMP-Cys or AMPD-Cys molar ratio of 5 to 1 and left for stirring in the dark for another 7 days at 45° C. Before being lyophilized for storage, the polymer solution was purified and washed by dialysis in Amicon tubes in order to remove any unreacted reagents. The degree of grafting was measured by amino acid analysis (AAA).

For the addition of $A_1$, $A_2$ or $A_3$ to the reaction mixture, it is important to add TCEP as a reducing agent. This step is required to prevent the formation of dimers of AMPDs-Cys. Applicant could see as well that the best reaction time for $A_3$ coupling to chitosan derivatives is up to 7 days for a better degree of grafting.

To Applicants' best knowledge, this is the first attempt to couple AMPDs to chitosan derivatives, reaching the same, even lower MIC of AMPD alone, without toxicity to HDF. Applicants provide here a controlled grafting of AMPDs-Cys or linear AMPs-Cys with a library of 7 sulfo-crosslinkers and 2 scaffold biopolymers (Table 2 and 3).

TABLE 2

Degree of substitution (w/w %), MIC (µg/mL); synergy effect; yield (mass %) and the solubility of $G_3KL$-Cys coupled through 7 different sulfo-crosslinkers ($L_1$-$L_7$) to 2 scaffold polymers ($C_1$ and $C_2$).

|  | $A_3L_1C_1$ $A_3L_1C_2$ | $A_3L_2C_1$ $A_3L_2C_2$ | $A_3L_3C_1$ $A_3L_3C_2$ | $A_3L_4C_1$ $A_3L_4C_2$ | $A_3L_5C_1$ $A_3L_5C_2$ | $A_3L_6C_1$ $A_3L_6C_2$ | $A_3L_7C_1$ $A_3L_7C_2$ |
|---|---|---|---|---|---|---|---|
| DS | 18.2 | 17.9 | 15.7 | 25.3 | 17.1 | 22.6 | 17.8 |
| (w/w %) | 18.9 | 17.2 | 20.8 | 13.0 | 18.2 | 18.4 | 25.3 |
| MIC (µg/mL) | 2.9 | 2.8 | 1.3-2.5 | 4.0-8.0 | 5.5 | 1.8-3.6 | 2.8-5.6 |
|  | 3.0-6.0 | 2.8-5.6 | 3.3 | 4.2 | 2.9-5.8 | 2.9-5.8 | 4.0-8.0 |
| Synergy effect | Strong | Strong | Very Strong | Strong | Synergy | Strong | Strong |
|  | Strong | Strong | Strong | Strong | Strong | Strong | Strong |
| Yield (w %) | 33.4 | 50.2 | 24.0 | 28.1 | 36.8 | 62.1 | 76.2 |
|  | 54.2 | 66.1 | 71.7 | 37.4 | 75.8 | 61.4 | 89.7 |
| Solubility | +++ | +++ | ++++ | +++ | + | ++ | ++++ |
|  | + | + | +++ | + | + | + | + |

Single letter code:

[C] for chitosan derivative;

[L] for crosslinkers and

[A] for AMPD-Cys.

More detailed, $C_1$ = CMTMC;

$C_2$ = CMC;

$L_1$ = sulfo-SMCC;

$L_2$ = sulfo-SMPB;

$L_3$ = sulfo-GMBS;

$L_4$ = sulfo-EMCS;

$L_5$ = sulfo-KMUS;

$L_6$ = sulfo-LC-SPDP;

$L_7$ = sulfo-SIAB and $A_3$ = $G_3KL$-Cys AMPD.

Solubility scale:

"+" = poorly soluble;

"++" = partial soluble;

"+++" = very soluble;

"++++" = completely soluble.

Synergy values were calculated using fractional inhibitory concentration index (FTC) method based on Chou-Talalay method [5].

The synergy obtained from FIC was defined as: Very strong synergism defined for FTC of <0.1; strong synergism for FIC 0.1-0.3; synergism for FIC 0.3-0.7; moderate synergism for FIC 0.7-0.85; slight synergism for FTC 0.85-0.9; nearly additive for FTC 0.9-1.1; slight antagonism for FTC 1.1-1.2; moderate antagonism for FTC 1.2-1.45; antagonism for FTC 1.45-3.3; strong antagonism as FTC 3.3-10; very strong antagonism for FTC>10.

Based on the results provided in Table 2, the best cross-linkers with the best MIC and solubility are the $L_3$ and $L_7$, which are sulfo-GMBS and sulfo-SIAB respectively, as referred in FIG. 4. Moreover, the antibacterial activity of $A_3$ is preserved during the reaction with any of the crosslinkers or chitosan backbone. The MIC for native $G_3KL$ is 8-16 μg/mL [3,6]. Interestingly, $G_3KL$-Cys coupled to the new platform has even lower MICs, which leads to the conclusion that AMPD/AMP and chitosan have an antibacterial synergistic effect.

Further, having selected the best candidates for $G_3KL$-Cys coupling ($L_3$ and $L_7$), Applicants could perform the coupling of $A_2$ and $A_1$ on CMTMC and CMC backbone (Table 3).

TABLE 3

Degree of substitution (w/w %), MIC (μg/mL); synergy effect; yield (mass %) and the solubility of $A_2$ and $A_1$ coupled through 2 selected sulfo-crosslinkers ($L_3$ and $L_7$) to 2 scaffold polymers $C_1$ and $C_2$.

|  | $A_1L_3C_1$ / $A_1L_3C_2$ | $A_2L_3C_1$ / $A_2L_3C_2$ | $A_1L_7C_1$ / $A_1L_7C_2$ | $A_2L_7C_1$ / $A_2L_7C_2$ |
|---|---|---|---|---|
| DS (w/w %) | 23.5 / 25.0 | 16.7 / 32.6 | 21.5 / 25.7 | 22.6 / 31.5 |
| MIC (μg/mL) | 8.0 / 7.5 | >83.5 / 10.7 | 4.1-8.2 / 13.8 | 80.6 / 28.9 |
| Synergy effect | Synergy / Synergy | Slight / Very strong | Strong / Slight | Moderate / Strong |
| Yield (w %) | 33.4 / 54.2 | 50.2 / 66.1 | 24.0 / 71.7 | 28.1 / 37.4 |
| Solubility | ++++ / ++++ | +++ / ++++ | ++++ / ++++ | ++++ / +++ |

Single letter code:
[C] for chitosan derivative;
[L] for crosslinkers and
[A] for AMPD-Cys.
Specifically,
$C_1$ = CMTMC;
$C_2$ = CMC;
$L_3$ = sulfo-GMBS;
$L_7$ = sulfo-SIAB;
$A_2$ = $G_2$KL-Cys AMPD and
$A_1$ = RH9L-Cys AMP.
Solubility scale:
"+" = low soluble;
"++" = partial soluble;
"+++" = soluble;
"++++" = completely soluble.

The results presented in Table 3 show that the conjugation based on chitosan backbone can be carried out with second (AMPD) and first (AMP) generation peptides without altering the antibacterial activity of these peptides. The MIC of $G_2KL$=64-128 μg/mL; RH9L=4 μg/mL [7]. Still, the best crosslinker for preserving the antibacterial activity is $L_7$ for CMTMC and $L_3$ for CMC based polymers.

Furthermore, the synergistic effect of the covalent coupling to either CMTMC or CMC chitosan derivatives is demonstrated in Table 2 for $3^{rd}$ generation peptide $A_3$ and Table 3 for $A_1$ and $A_2$ peptides. Computation of synergy is based on classical Chou-Talalay approach [5,8]. The MIC of CMTMC and CMC alone were >2048 μg/mL and 2048 μg/mL, respectively.

The calculated FIC shows that synergies are always observed for the covalent chitosan-AMPDs-Cys, ranging from slight synergy, in one case, to strong or very strong synergy, in most of the cases. This unexpected result underlines the potential of the invention to enhance peptide antimicrobial potency.

Materials for Example 1

Chitosan (81% degree of deacetylation, ChitoClear Cg10, 8 mPa·s, Primex, Siglufjördur, Iceland). Chloroacetic acid, methyl iodide (99%), N-methyl-2-pyrrolidone (NMP) (99%) and 1,6-diaminohexane (DAH) were purchased from Sigma-Aldrich (Buchs, Switzerland). Sodium hydroxide (98.5%) and N-hydroxysulfosuccinimide sodium salt (95%) (sulfo-NHS) were acquired from Acros Organics (Geel, Belgium). Sulfo-SIAB was obtained from Brunschwig (Basel, Switzerland); sulfo-SMCC, sulfo-SMPB, sulfo-GMBS, sulfo-EMCS, sulfo-KMUS and sulfo-LC-SPDP were purchased from Sigma Aldrich, Switzerland. AMPDs-Cys: $G_3KL$-Cys and $G_2KL$-Cys and AMP-Cys: RH9L-Cys were synthesized in Applicant's labs following previous protocols [6]. Amicon Ultra-15 Centrifugal Filter Units with a 10 kDa cut-off were obtained from Merk Millipore (Darmstadt, Germany).

Method 1 for Example 1: $^1$H-NMR $^1$H-NMR spectra were recorded using a Bruker Avance III HD 600 MHz spectrometer equipped with a QCI 5 mm Cryoprobe and a SampleJet automated sample changer (Bruker BioSpin, Rheinstetten, Germany). NMR spectra prediction was performed using Mnova software V10.0.2 (MestreNova, Santiago de Compostela, Spain). All analyses were run at room temperature. $^1$H chemical shifts were reported as parts per million (ppm). The polymers were dissolved in $D_2O$ containing 1% DCl.

Method 2 for Example 1: Amino Acid Analysis (AAA)

AAA was done by vacuum-hydrolysis over 22 hours in 6M HCl and 0.1% phenol [9]. Briefly, the samples (1-10 μg) were transferred in a hydrolysis tube and then 5 μL of Titriplex III solution (2 mg/mL) was added. The samples were dried in a Speed-Vac. Then, 200 μL of 6M HCl was pipetted to the hydrolysis vessel. The tube was then transferred to the hydrolysis vessel and the vessel was dried under vacuum with $N_2$. At the end, a vacuum of 20-40 mm Hg was applied. The vessel was then heated at 115° C. in a heat block for 22 hours. After hydrolysis, the vessel was immediately vented and the sample was dried in a Speed-Vac and then coupled to phenyl isothiocyanate. Afterwards, the samples were dried and quantified by HPLC [9].

Method 3 for Example 1. MIC with Polymers Alone on *P. aeruminosa*

Antibacterial activity of AMPs/AMPDs alone and coupled was assessed against *P. aeruginosa* (clinical isolates, ATCC 27853). Colonies of bacteria were grown in Mueller Hinton Broth (MHB) medium overnight. $A_1$, $A_2$ and $A_3$-S—$C_2$ $A_1$, $A_2$ or $A_1$, $A_2$ and $A_3$-S—$C_2$ polymers were prepared in MHB as stock solution at 2048 μg/mL. 100 μL stock solution was added to the first well of a 96-well plate and diluted successively by ½, keeping as well, positive (broth with bacteria) and negative (sterile broth medium) controls and a blank (non-derivatized polymer alone, like $C_1$ and $C_2$). Afterwards, equal amount of bacterial suspension ($5×10^5$ CFU) in broth was added to the sample solutions in microplates. The plates were incubated for 24 h to allow bacterial growth and the bacterial concentration was read at 600 nm by diluting the growth medium in MHB at 1:100. All samples were run in triplicates and the MIC was established as the lowest concentration of the $A_1$, $A_2$ and $A_3$-S—$C_2$ $\lambda 1$, $A_2$ or $A_1$, $A_2$ and $A_3$-S—$C_2$ resulting in bacterial death. The MIC for the active principles: $A_1$, $A_2$ and $A_3$ was calculated according to their degree of substitution from AAA data reported.

Example 2: Mechanism of Action as Observed by TEM, Vesicle Leakage Assay and Circular Dichroism TEM imaging showed that $A_3$-S—$C_1$ polymer is a membrane-disruptive compound. Compared to conventional antibiotics prescribed in the hospital like Polymyxin B, both native $G_3$KL AMPD and $A_3$-S—$C_1$ attack both inner and outer bacterial membranes. This is not the case for Polymyxin B, which attacks only the outer membrane of the bacteria (Table 4). It appears that the mode of action of the peptide does not seem to be modified upon chitosan grafting. This is confirmed by the vesicle leakage assay, outlining a similar mechanism of action for the peptide alone and the chitosan-couple peptide (FIG. 8). Furthermore, the covalent coupling strategy did preserve the helical structure of the peptide, as confirmed by circular dichroism studies.

TABLE 4

TEM results of *P. aeruginosa* (PA01) treated with G3KL, $A_3$-S-$C_1$ and Polymyxin B.

| Compound | Concentration (μg/mL) | Effect on *P. aeruginosa* (PA01) |
| --- | --- | --- |
| G3KL | 40 | Attack on the inner and outer membrane |
| $A_3$-S-$C_1$ | 40 | Attack on the inner and outer membrane |
| $A_3$-S-$C_1$ | 64 | More pronounced effect on both inner and outer membrane |
| Polymixin B | 5 | Attack on the outer membrane |

Method 1 for Example 2: Transmission Electron Microscopy (TEM) with $A_3$-S—C1 on *P. aeruginosa*

*Pseudomonas aeruginosa* PAO1 in the exponential phase were washed with phosphate buffered saline (PBS) and treated with 5 μg/mL Polymyxin B, 40 μg/mL $G_3$KL and 40 or 64 μg/mL $A_3$-S—$C_2$ in M63 minimal medium. Each time, 1 ml of the bacteria were centrifuged after 15, 30 and 60 min at 12'000 rpm for 3 min and fixed overnight with 2.5% glutaraldehyde (Agar Scientific, Stansted, Essex, UK) in 0.15 M HEPES (Fluka, Buchs, Switzerland) with an osmolarity of 670 mOsm and adjusted to a pH of 7.35. The next day, PAO1 were washed with 0.15 M HEPES three times for 5 min, post fixed with 1% $OsO_4$ (SPI Supplies, West Chester, USA) in 0.1 M Na-cacodylate-buffer (Merck, Darmstadt, Germany) at 4° C. for 1 h. Thereafter, bacteria were washed in 0.1 M Na-cacodylate-buffer three times for 5 min and dehydrated in 70, 80, and 96% ethanol (Alcosuisse, Switzerland) for 15 min each at room temperature. Subsequently, they were immersed in 100% ethanol (Merck, Darmstadt, Germany) three times for 10 min, in acetone (Merck, Darmstadt, Germany) two times for 10 min, and finally in acetone-Epon (1:1) overnight at room temperature. The next day, bacteria were embedded in Epon (Fluka, Buchs, Switzerland) and hardened at 60° C. for 5 days.

Sections were produced with an ultramicrotome UC6 (Leica Microsystems, Vienna, Austria), first semi thin sections (1 um) for light microscopy which were stained with a solution of 0.5% toluidine blue 0 (Merck, Darmstadt, Germany) and then ultrathin sections (70-80 nm) for electron microscopy. The sections, mounted on single slot copper grids, were stained with uranyl acetate and lead citrate or UranyLess (Electron Microscopy Sciences, Hatfield, UK) at 40° C. for 10 minutes and 3% lead citrate at 25° C. for 10 minutes with an ultrostainer (Leica Microsystems, Vienna, Austria).

Sections were then examined with a Tecnai Spirit TEM equipped with two digital cameras (Olympus-SIS Veleta CCD Camera, FEI Eagle CCD Camera).

Method 2 for Example 2. Vesicle Leakage Assay

This assay was modified from a previously reported protocol [9]. Egg phosphatidylcholine (PC) or Egg phosphatidylglycerol (PG) thin lipid layer was prepared by evaporating a solution of 100 mg Egg PC or Egg PG in 4 mL MeOH/$CHCl_3$ (1:1) on a rotary evaporator at room temperature and then in vacuo overnight. The resulting film was hydrated with 4 mL buffer (50 mM 5(6)-carboxyfluorescein (CF), 10 mM TRIS, 107 mM NaCl, pH 7.4) for 30 min, subjected to freeze-thaw cycles (7×) and extrusion (15×) through a polycarbonate membrane (pore size 100 nm). Extra vesicular components were removed by gel filtration (Sephadex G-50) with 10 mM TRIS, 107 mM NaCl, pH 7.4 buffer. Final conditions: ~2.5 mM Egg PC or Egg PG; inside: 50 mM CF, 10 mM TRIS, 10 mM NaCl, pH 7.4 buffer; outside: 10 mM TRIS, 107 mM NaCl, pH 7.4 buffer.

Egg PC or Egg PG stock solutions (37.5 μL) were diluted to ~3000 μL with a buffer (10 mM TRIS, 107 mM NaCl, pH 7.4) and the compound of interest was pipetted in a thermostat fluorescence cuvette (25° C.) and gently stirred (final lipid concentration ~31 μM). CF efflux was monitored at $\lambda_{em}$ 517 nm ($\lambda_{ex}$ 492 nm) as a function of time after the addition of the correct volume of the peptide dendrimer $G_3$KL-Cys or $L_7C_1A_3$ dissolved in mQ water. The final concentrations of the peptide dendrimer was 1, 5, 10, 20 μg/mL at t=50 s. 1.2% Triton X100 30 μL was added to cuvette (0.012% final concentration) at t=300 s. Fluorescence intensities were normalized to fractional emission intensity I(t) using I(t)= $(I_t-I_0)/(I_\infty-I_0)$ where $I_0$ $I_t$ at peptide dendrimer addition, $I_\infty=I_t$ at saturation of lysis.

Method 3 for Example 2. Circular Dichroism (CD)

CD spectra were recorded using a Jasco J-715 spectrometer equipped with a PFD-350S temperature controller and a PS-150J power supply. All experiments were measured using a Hellma Suprasil R 100-QS 0.1 cm cuvette. Stock solution (1 mg/mL) of the AMP/AMPD-chitosan derivatives were freshly prepared in mQ-deionized water. For the measurements, the compounds were diluted to 200 μg/mL with phosphate buffer and TFE. The range of measurement was 190-260 nm, scan rate was 10 nm/min, pitch 0.5 nm, response 16 sec and band 1.0 nm. The nitrogen flow was kept above 8 L/min. The blank was recorded under the same conditions and subtracted manually. Each sample was subjected to two accumulations. The cuvettes were washed with 1M HCl, mQ-H2O and PB buffer before each measurement [10].

Example 3: Cytocompatibility of the Chitosan-AMPs

The biocompatibility of $A_3$-S—$C_1$ (using $L_7$) was evaluated against control cells (HDF—positive control) and SDS (negative control) at different time points. Surprisingly, concentrations up to 3×MIC (at day 4) or 5×MIC (at day 2) were well tolerated by HDF, without decreasing mitochondrial activity (FIG. 5). In a hospital setup, where these bandages have to be changed every 2-3 days, the data shows a potentially useful therapeutic window.

Moreover, the obtained polymer was evaluated for the presence of endotoxin with a ToxinSensor Gel Clot Endoxin assay kit from GenScript (No. L00351) and was endotoxin-free at concentrations <0.25 EU/mL. This level complies with topical application on skin, as well as wounds as stated in European Pharmacopoeia 5.0.

Method 1 for Example 3. Biocompatibility Assay of HDF Treated with $A_3$-S—$C_1$ HDF (human dermal fibroblasts, progenitor cells, 12 weeks male donor, Ethics Committee Protocol #62/07, Lausanne, Switzerland) were seeded in a 96-well plate (Corning®, USA) at a density of $2 \times 10^3$ cells/mL. After incubation for 48 h, DMEM was replaced by 100 µL of $A_3$-S—$C_2$ suspension at concentrations of 1, 3, 5, 6 and 7 minimal inhibitory concentration (MIC), respectively. Mitochondrial activity in the cells was evaluated at day 2 and 4. Sodium dodecyl sulfate (SDS) (1%) and DMEM treated cells (DMEM supplemented with 10% fetal calf serum (FCS)) were used as negative or positive control, respectively. After day 2 or 4, the supernatant (the polymer suspension) on top of the cells was removed and 100 µL WST-1 (Roche, Switzerland), was added in each well at 1:10 dilution in DMEM and incubated for 1.5 h. Absorbance values were read with BioTek Microplate (GmbH, Luzern, Switzerland) at two different wavelengths (450 and 690 nm). The mitochondrial activity is presented as percentage compared to the positive control group (cells in DMEM supplemented with 10% FCS). All experiments were carried out in triplicates.

Formulations Examples

Formulations were investigated using the $3^{rd}$ generation peptide dendrimer chitosan derivatives $A_3$-S—C coupled through $L_3$ crosslinker. In addition, the CMC (purchased from Heppe Medical HMC⁺, Germany) and HA were used to formulate gels and foams. Both CMC and HA acted as matrix for incorporating active principle: $A_3$-S—C for topical application.

Example 4: Nanoparticles (NPs)

Preparation of Nanoparticles (NPs) Formulation

Freeze-dried $A_3$-S—$C_1$ or $A_3$-S—$C_2$/CS NPs were prepared by "one-shot" method mixing positively charged $G_3$KL-Cys-DAH-CMTMC or $G_3$KL-Cys-DAH-CMTC with a negatively charged polymer such as CS, as follows.

First, $A_3$-S—$C_1$ or $A_3$-S—$C_2$ and CS polymers were separately dissolved at different mass ratios in water (w/V). $A_3$-S—$C_1$ or $A_3$-S—$C_2$ were separately dissolved in water to reach a concentration of 5 mg/mL (w/v) and CS added to reach a range concentration between 0.5-5 mg/mL (w/v). All polymer solutions were filtered through 0.22 µm filter before use. The polymers were mixed together at the same volumetric ratios (1:1 v/v) in an Eppendorf tube. The obtained dispersion was vortexed for 10 sec followed by centrifugation (Eppendorf AG 22331, Hamburg) at 3220×g for 10 mins at 10° C. for separating NPs. Later, the supernatant was discarded and only the pellets retained (the NPs). NPs were re-suspended in water or trehalose 1% in an Eppendorf tube followed by freeze-drying at −80° C. using a Christ Alpha 2-4 LD plus lyophilizer (Kuehner AG, Birsfelden, Switzerland). Trehalose acts as a cryoprotectant for NPs.

For aqueous stability reasons, NPs were characterized by DLS for their particle size, polydispersity index and zeta potential. For long-term storage, NPs were stored in water or trehalose 1% and evaluated immediately or after being stored at 4° C. for different time points. The morphology of the NPs was assessed by scanning electron microscopy (SEM; JEOL JSM-7001FA, Tokyo, Japan) at 5 kV and coated with 10 nm gold.

Characterization: Size, Zeta Potential, Stability

Mixing two oppositely charged polymers at different ratios lead to either anionic (−50 mV zeta potential) or cationic (+25 mV) NPs within different PDIs depending on $A_3$-S—$C_1$/CS ratio. Negatively charged (−50 mV) NPs with a small size and narrow distribution can be obtained using mass ratios higher than 5:3.

In case of $A_3$-S—$C_2$/CS, cationic NPs (between +16 and +40 mV) NPs were obtained using mass ratios 5:1, as shown in Table 5.

TABLE 5

Formation of NPs between $A_3$-S-$C_1$ or $A_3$-S-$C_2$ and CS at different ratios (w/w) with different zeta potential, sizes and PDI.

| $A_3$-S-$C_1$/CS $A_3$-S-$C_2$/CS | ZP (mV) | Z-average (nm) | PDI |
|---|---|---|---|
| 5 to 1 | 21.4 ± 0.3 | >6075 | 1 |
|  | 38.6 ± 0.9 | 216 ± 4.3 | 0.3 |
| 5 to 2 | −13.6 ± 0.4 | 473.4 ± 9.2 | 1 |
|  | 32.8 ± 0.6 | 225 ± 2.7 | 0.2 |
| 5 to 3 | −36.2 ± 0.4 | 209.3 ± 1.7 | 0.4 |
|  | 27.2 ± 0.9 | 307 ± 10.1 | 0.3 |
| 5 to 4 | −38.5 ± 0.3 | 207.7 ± 1.9 | 0.1 |
|  | 22.8 ± 1.3 | 971 ± 18.9 | 0.7 |
| 5 to 5 | −50.5 ± 4.1 | 204.0 ± 1.4 | 0.1 |
|  | 15.8 ± 3.2 | 7822 ± 14.4 | 0.7 |

For long-term storage, NPs were cryoprotected with trehalose 1% (w/w) over 1 month.

Anionic NPs ($A_3$-S—$C_1$/CS) with ratio 5:5 proved to be very stable when stored during and after lyophilization in 1% trehalose even after 3 weeks, probably due to high zeta potential. They kept the same size (±210 nm) and a narrow distribution (PDI=0.3) of the NPs. NPs in water or in PBS behaved differently than in trehalose for both short and long term storage. Upon lyophilization and resuspension in PBS, all NPs aggregated showing lack of colloidal stability. However, 1% trehalose stabilized all the particles, showing that lyophilization with trehalose cryoprotectant is an adequate method for long-term storage of the formulation. Data were confirmed by SEM as well.

Biocompatibility HDF Exposed to NPs

HDF were treated as described in Method 6 for Example 1. Freshly prepared NPs ($A_3$-S—$C_1$/CS) (described in Example 2) were suspend in DMEM (serum-free) at 1:1 (v/v) ratio and 100 µL NPs suspension was exposed to HDF. Viability assay showed the safety of NPs towards fibroblasts (FIG. 6). HDF were exposed to NPs (ratio 5:5) for 24 h containing 1 and 2×MIC of $G_3$KLC.

NPs Bioactivity (MIC Assay)

Interestingly, the MICs of AMPD-tailored NPs dropped with the increase of CS concentration ($A_3$-S—$C_1$/CS) (FIG. 7). These results proved that the activity of AMPD is hindered by the addition of CS. However, cationic NPs are most effective against *P. aeruginosa*. Corresponding MIC for $G_3$KL incorporated into NPs is 33.3 µg/mL (for ratios 5:1; 5:1.5; 5:2), which is higher when compared to the MIC of the native $G_3$KL.

Example 5: Gel-Like Formulations

Preparation of Gel-Like Formulations

A $A_3$-S—$C_1$/HA/CMC or $A_3$-S—$C_2$ gel for topical application was prepared as follows.

First, each polymer: CMC (powder form from Heppe); HA (sodium hyaluronate; 1.9 MDa powder form from HTL, France) and $A_3$-S—$C_1$ or $A_3$-S—$C_2$ (powder synthesized as described in Example 1) was solubilized in NaCl 0.9% to reach the following concentrations: CMC 1-6%; HA 1% and a known weight of $A_1$; $A_2$; $A_3$-S—$C_1$ or $A_3$-S—$C_2$ was added to CMC/HA mixture to reach final concentrations of 1-10×MIC. CMC and HA were added at the same volume ratios (1:1) and stirred overnight at ambient temperature (+22° C.).

Herein, CMC and HA act as a matrix and $A_3$-S—$C_1$ or $A_3$-S—$C_2$ as an active principle inside the hydrogels.

Rheological analysis using a Rheostress 1 Haake rheometer with a cone-plate geometry cone (35 mm/2° Ti, Vreden, Germany) thermostated with a circulating bath at 37° C. at a shear rate range 0-3600 $s^{-1}$. The viscosity for the gel-like formulations was around 0.1 Pa·s.

Example 6: Bandage-Like Formulations

Preparation of Bandage-Like Formulations

A $A_3$-S—$C_2$/HA/CMC or $A_3$-S—$C_2$/HA/CMC bandage for topical application was prepared as described in Example 3, but with addition of a lyophilization step, leading to solid foam-like bandages.

A known amount of hydrogel mixture was poured into homemade stainless molds with sizes 1×3; 3×3; 4×4 cm, special designed for lyophilization of gels into foams. Molds containing hydrogels are then placed into a lyophilizer (TelStar LyoBeta-15, Spain) for freeze-drying process. Shelves are slightly cooled at 20° C., then freezed to −40° C. during 2 h. It is very important to have a control over the cooling rate to avoid foam cracking. Afterwards, primary drying is done for 10 h at −40° C. and secondary drying for 9 h at 30° C. The resulting foams are uniform with a whitish appearance. Their thickness is +2 mm (n>20 batches).

The mechanical properties of the foam-like bandages were evaluated using a TA.XT Plus texture analyzer from Stable Micro System (Godalming, United Kingdom) at a speed of 1.2 mm/min. The compressive modulus was determined for each bandage. Each run was done in 5 replicates. The morphology of these foams was assessed by SEM at 5 kV and coated with 10 nm gold. Lyophilized foams showed a porous structure, as confirmed by SEM. As well, they were flexible and non-brittle, with the same texture as conventional bandages, which proves their suitability for topical application.

Method 1 for Example 4. Foam Characterization: SEM and Texture Analyser

Lyophilized foams were obtained after the freeze-drying process. Depending on the concentration of the polymers, we obtained ready-to-use foams. All foams with CMC concentrations below 4% were brittle and above 6%, all foams were very rigid and with too many bubbles, indicating non-homogeneous distribution of the polymers. Foams with a blend of 4% CMC/1% HA were selected for further studies as they had a smooth surface, with uniform edges. Moreover, SEM images indicated a homogeneous distribution of the pores inside the matrix.

Method 2 for Example 4. Biocompatibility Assay on HDF

An $A_1$, $A_2$ and $A_3$-S—$C_2$ $A_1$, $A_2$ or $A_1$, $A_2$ and $A_3$-S—$C_2$ foam was prepared as described in Example 3.

From each resulting foam, a piece of 1×1 cm was cut and fixed to the bottom of the well from a 6-well plate with a metallic insert. Afterwards, on top of the foams a known volume of DMEM or PBS was placed to dissolve the foams. HDF were seeded on top or around the different foams at an initial density of 3000 or 6000 cells/$cm^2$. All experiments were run in triplicates for each condition. Cell viability was assessed using Giemsa staining at 2 time points: Day 5 and 7 to reach full cell confluence.

4. Conclusions

The present invention combines different length AMPs/AMPDs as bioactive peptides with a biopolymer vehicle through 7 sulfo-crosslinkers to enhance the bioactivity of the antimicrobial peptides AMPs/AMPDs.

Applicants target to have an efficient delivery of the bioactive dendrimer peptide to the wound site, which prevents infection, restoring tissue healing. More specifically, the ability to deliver the peptide in a sustained manner can prevent infection over the time-needed regeneration. The nanocomplexes protect the peptide from the degradation usually occurring in wound exudates.

Surprisingly, covalent grafting of big AMPD to chitosan did not disturb its bioactivity towards *P. aeruginosa*; moreover, Applicants have observed a clear synergistic effect for the bio-conjugate of the invention. On top of preserving its bactericidal effect, the new synthesized molecules have no toxicity towards HDF at a 5-fold MIC.

Applicants were suspecting that using smaller AMPDs, one might not reach sufficient charge density to ensure peptide activity. On the contrary, the Applicants demonstrated that smaller AMPD (such as $G_2KL$) or linear AMPs are also active as conjugates and even shown increased and synergistic antibacterial activity towards *P. aeruginosa* upon conjugation.

Chitosan coupling to AMP/AMPDs-Cys reduces the side effects of using AMPDs alone, like decreased toxicity while being able to kill the bacteria; ease of topical application in different delivery ways: as NPs, hydrogels or foams.

Additional ability of the dressing to guide and promote tissue regeneration further enhances and/or accelerates the process of wound healing.

Example 7: Fabrication and Bioactivity of Additional Chitosan Derivatives for AMP Conjugation Description: This example discloses the fabrication of additional chitosan derivatives, which can be coupled to AMPs. The antimicrobial activity of these additional conjugates confirms the potentiation of the bioactivity occurring upon conjugation of the AMP with chitosan derivatives, as demonstrated by the synergy measured for all conjugates excepted the RH9L-CMMPyMeC.

N-(4-pyridylmethyl) (PyMeC) and N-(4-N,N-dimethyl-amino-cinnamyl) (DMCMC) Chitosan Synthesis PyMeC and DMCMC chitosan derivatives were synthetized following the protocol of Sajomsong et al. with some modifications (Sajomsang et al., Carbohydr Res. 2009; 344(18):2502-2511). Briefly, 1 g of chitosan was dissolved in 70 mL of 0.2 M acetic acid. Subsequently, 70 mL of ethanol was added and mixed at room temperature for 1 h. Then, 0.29 µl of 4-pyrridine-carboxyaldehyde, or 0.54 g of 4-N—N-dimethyl-amino-cinnamaldehyde, was added and stirred, under reflux at 60° C. for 15 h and the pH adjusted to 5. Subsequently, 16 mL of sodium cyanoborohydride (NaCNBH; 96.25 µg/L) were added dropwise to chitosan solution and stirred for 24 h. Afterwards the pH was adjusted to 12 and the precipitate was collected and dissolved in Milli-Q water. Dialysis was run for 3 days using Spectra/Por dialysis membrane with a molecular cut-off of 12-14 kDa. The first day was done against 1% NaCl and the last 2 days against distilled water. Finally, the compound was freeze-dried for 3 days and analysed by FTIR and $^1$H-NMR.

Methylation of PyMeC and DMCMC

N-aryl derivatives, methyl-DMCMC (MDMCMC) and methyl-PyMeC (MPyMeC) were synthesized following Sajomsang et al. with some modifications (Sajomsang et al., Eur Polym J 2009; 45(8):2319-2328). Therefore, 1 g of N-aryl derivative (DMCMC or PyMeC chitosan) was added to 50 mL of NMP and mixed at room temperature for 12 h. Then, 8 mL of NaOH 15% (w/v) together with 3 g of sodium iodide (NaI) were added and mixed under reflux at 60° C. for 15 min. Subsequently, 8 mL of methyl iodide were added to the solution and left to react at 60° C. for 24 h. After polymer precipitation in acetone, the precipitate was dissolved in 15% NaCl and dialyzed for 3 days (the first day against 1% NaCl and day 2 and 3 against deionized water. Lyophilization was performed for 3 days followed by NMR and FTIR analysis.

Carboxylation of MDMCMC and MPyMeC

The carboxylation step for MPyMeC and MDMCMC was similar to Example 1 (DAH-CMTMC synthesis (S—$C_1$)) to obtain final polymers carboxymethylated MDMCMC (CMDMCMC) or carboxymethylated MPyMeC (CMPyMeC).

CMDMCMC and CMPyMeC Coupling to AMP/AMPDs

AMP/AMPDs grafting to the CMDMCMC or CMPyMeC was similar to Example 1.

It starts with addition of DAH spacer to CMDMCMC or CMPyMeC resulting with two different final polymers: DAH-CMDMCMC and DAH-CMPyMeC. DAH spacer was grafted to chitosan derivatives following Example 1.

AMP/AMPDs were added to both DAH-CMDMCMC and DAH-CMPyMeC as shown in Example 1.

TABLE 6

Degree of substitution (w/w %), MIC (µg/mL); synergy effect; yield (mass %) and the solubility of $G_3$KL-Cys coupled through sulfo-SIAB sulfo-crosslinkers ($L_7$) to 2 scaffold polymers ($C_3$ and $C_4$).

|  | $A_3L_7C_3$ $A_3L_7C_4$ | $A_2L_7C_3$ $A_2L_7C_4$ | $A_1L_7C_3$ $A_1L_7C_4$ |
|---|---|---|---|
| DS (w/w %) | 10.2 | 10.6 | 13.9 |
|  | 25.7 | 10.3 | 12.4 |
| MIC | 3.3 | 13.6 | 17.9 |
| (µg/mL) | 16.5 | 13.2 | 7.9 |
| Synergy effect | Strong synergy Nearly additive | Strong synergy Strong synergy | Slight antagonism Synergy |
| Yield (w %) | 99 | 78.8 | 99.8 |
|  | 99.9 | 59.9 | 98.9 |
| Solubility | ++ | ++ | + |
|  | + | ++ | ++ |

Single letter code:
[C] for chitosan derivative;
[L] for crosslinkers and
[A] for AMPD-Cys.
More detailed,
$C_3$ = CMPyMeC;
$C_4$ = CMDMCMC;
$L_7$ = sulfo-SIAB;
$A_3$ = $G_3$KL-Cys;
$A_2$ = $G_2$KL-Cys and
$A_1$ = RH9L-Cys AMPD.
Solubility scale:
"+" = poorly soluble;
"++" = partially soluble;
"+++" = very soluble;
"++++" = completely soluble.

Example 8: Covalent Coupling of Commercially Available AMPs

Description: This example shows that the principle of AMP conjugation with the chitosan derivatives CMTMC and CMC can be further extended to AMPs of commercial interest.

AMPs' grafting to the CM-TMC or CMC was carried out according to Example 1.

It starts with addition of DAH spacer to CMDMCMC or CMPyMeC resulting with two different final polymers: DAH-CMTMC and DAH-CMC. DAH spacer was grafted to chitosan derivatives following Example 1. OP-145; His-1; LL-37 and IDR-1018 AMPs were added to both DAH-CMTMC and DAH-CMC as shown in Example 1.

TABLE 7

Degree of substitution (w/w %) of $G_3$KL-Cys coupled through sulfo-SIAB sulfo-crosslinkers ($L_7$) to 2 scaffold polymers ($C_3$ and $C_4$).

|  | $A_4L_7C_1$ $A_4L_7C_2$ | $A_5L_7C_1$ $A_5L_7C_2$ | $A_6L_7C_1$ $A_6L_7C_2$ | $A_7L_7C_1$ $A_7L_7C_2$ |
|---|---|---|---|---|
| DS (w/w %) | 9.1 | 2.9 | 11.1 | 4.7 |
|  | 42.9 | 1.5 | 5.8 | 2.5 |

Single letter code:
[C] for chitosan derivative;
[L] for crosslinkers and
[A] for AMP-Cys.
More detailed,
$C_1$ = CMTMC;
$C_2$ = CMC;
$L_7$ = sulfo-SIAB;
$A_4$ = OP-145-Cys;
$A_5$ = IDR-1018-Cys;
$A_6$ = LL-37-Cys and
$A_7$ = His-1-Cys AMPs.

Example 9: Long-Term Preservation of Antimicrobial Activity in a Biological Buffer Description: This example demonstrate that, besides synergistic potentiation of the AMP activity, conjugation with chitosan derivatives preserve the antimicrobial activity on the long term (months). This property represents an important asset to ensure a sustained antimicrobial action when applied for example to a patient's wound.

The stability of the parent peptide $G_3$KL has been shown previously (Darbre et al. 2014; PCT/EP2015/056819) to be limited to less than 24 hours in 25% human serum diluted with DMEM. The long-term preservation of antibacterial activity of chitosan-conjugates was thus assessed after keeping $A_3$-S—$C_2$ conjugate in MHB solution for 3 months at 4° C. Following, the activity of $A_3$-S—$C_2$ $A_1$ was tested against *P. aeruginosa* as described in Method 3 for Example 1. The results showed that the activity of $A_3$-S—$C_2$ $A_1$ was maintained at the same MIC value as before storage in MHB, which is 4 µg/mL.

Example 10: In Vivo Proof of Efficacy Against *P. aeruginosa*

Description: The preliminary data obtained in vivo indicate the efficacy of the chitosan conjugate formulated as a foam bandage to control *P. aeruginosa* infection.

The in vivo experiment on a model of infected wound was performed (Burkatovskaya et al, Biomaterials 2006; 27:4157-4164) on mice. Briefly, a full thickness 5×5 mm dorsal wound was created at day 0 and approximately 5·10$^7$ fluorescent *P. aeruginosa* inoculated in each wound. Fluorescence imaging was performed at day 0 and day 1 to measure bacterial growth. Four treatment groups (8 animal each) were used: an alginate bandage control, a CMTMC chitosan control, $A_3$-S—$C_1$, and a reference antibiotic control, silver sulfadiazine. The results (FIG. 9) show that the AMP-chitosan conjugate could slow down bacterial growth in a manner similar to the control antibiotics at day 1, with a 2.4-fold reduction of the bacterial density compared to the conventional alginate bandage, or a 2-fold reduction compared to chitosan alone.

Example 11: Safety Assessment Through Hemolysis Assay

Description: A critical issue for clinical use of AMPs is their toxicity, specifically towards sheep red blood cells, as assessed by hemolysis tests. Results show extremely low haemolysis rates for all considered conjugates $A_3$-S—$C_{1-4}$; $A_2$-S—$C_{1-4}$; $A_1$-S—$C_{1-4}$. The concentrations at 10×MIC have been chosen as examples, as below these values an absence of hemolysis was seen for every conjugate.

The haemolysis assay was performed following the literature (Mishra et al. RSC Adv. 2015; 5(73):59758-59769) with a down-scaling to 50 µL. Samples ($A_3$-S—$C_{1-4}$; $A_2$-S—$C_{1-4}$; $A_1$-S—$C_{1-4}$) were prepared at an initial concentration of 2048 µg/mL in PBS (pH 7.4) and diluted serially by ½ in PBS in a flat bottom 96-well plate (Corning®, polystyrene, untreated). Then, 50 µL of each sample was added to 50 µL RBC solution in a round-bottom microplate (Corning®, polystyrene, untreated) and left for stirring (Orbit LS shaker, S2030-LS-B) at room temperature for 30 min. Following, centrifugation at 4000 rpm was performed. Following, 50 µL of the supernatant from each well was separately mixed with 250 µL of pure ethanol in a flat-bottom 96-well plate and the absorbance was recorded at 412 and 700 nm.

Red Blood Cells (RBCs) Preparation

In parallel, RBCs were prepared using defibrinated sheep blood (Oxoid Ltd. Thermo-Fischer). 200 µL of sheep blood were added to 1 mL of PBS, very gently mixed and centrifuged at 1500 rpm for 1-2 minutes. The plasma was discarded carefully with a pipette. The washing was repeated 2 times (until the colour of the supernatant was clear) and the erythrocyte pellets were re-suspended in 11 mL PBS and then freshly used for the assay.

Hemolysis results are represented in FIG. 10. Almost negligible hemolysis is observed in case of $A_3$-S—$C_1$ at a concentration of 10×MICs, the conjugate is much more active at lower concentrations before haemolysis occurs. Higher haemolytic response is observed for $A_2$-S—$C_2$ and $A_1$-S—$C_2$, but is still below the therapeutic concentration.

Example 12: Killing Mechanism and Kinetics for the Chitosan-Peptide Conjugate

Description: The conjugation of AMPs to the chitosan derivatives preserves the killing mechanism of the parent peptide, inducing a rapid permeabilization of bacterial membrane death.

Method 1. Time-Lapse Microscopy

Time-lapse microscopy were performed following Gan et al. 2019; 5(12):2164-2173. After focusing the cells, the movie was started and 40 µL/mL of $A_3$-S—C1 (fluorescently labelled to allow cell tracking) was added to the coverslip. Here, the Fluo-$A_3$-S—C1 was excited by using 488 nm laser. The uptake of the fluorescently labeled Fluo-$A_3$-S—$C_1$ (Green channel: chitosan conjugate uptake) and subsequent rapid bacterial death (red channel: propidium iodide uptake) is shown in FIG. 11.

Fluorescently labelled $A_3$-S—$C_1$ was rapidly uptaken within 10-15 min into the bacterial cells, which means that the AMPD-conjugate permeabilizes the outer membrane. Propidium iodide which shows the death of bacteria, was detected very fast (after 2 min-2 min 30 s) right after the apparition of the conjugate. Furthermore, it shows that the PI was taken up gradually after conjugates could permeabilise the membrane of the cell.

Method 2. Mechanism of Action as Observed by TEM

TEM analysis were performed in similarly as described in Method 3, Example 2. TEM imaging showed that all conjugates, namely $A_3$-S—$C_1/C_2/C_3/C_4$ are membrane-disruptive compounds, attacking both inner and outer membrane. The mechanism of action of chitosan-conjugates coupled to $G_3$KLC AMPD ($A_3$) assessed by TEM on *P. aeruginosa* is shown in FIG. 12. All $G_3$KL-chitosan derivatives have similar disruption as native $G_3$KL by disrupting the outer layer of bacteria and in turn leading to death.

REFERENCES

[1] M. Kolpen, C. J. Lerche, K. N. Kragh, T. Sams, K. Koren, A. S. Jensen, L. Line, T. Bjarnsholt, O. Ciofu, C. Moser, M. Kuhl, N. Hoiby, P. O. Jensen, Hyperbaric Oxygen Sensitizes Anoxic *Pseudomonas aeruginosa* Biofilm to Ciprofloxacin. Antimicrob. Agents Chemother. 61 (2017). doi.org/10.1128/aac.01024-17.

[2] D. I. Andersson, D. Hughes, J. Z. Kubicek-Sutherland, Mechanisms and consequences of bacterial resistance to antimicrobial peptides. Drug Resist. Updat. 26 (2016) 43-57. doi.org/10.1016/j.drup.2016.04.002.

[3] T. N. Siriwardena, A. Capecchi, B. H. Gan, X. Jin, R. He, D. Wei, L. Ma, T. Kohler, C. Van Delden, S. Javor, J. L. Reymond, Optimizing Antimicrobial Peptide Dendrimers in Chemical Space. Angew. Chem., Int. Ed. Engl. 57 (2018) 8483-8487. doi.org/10.1002/anie.201802837.

[4] V. Patrulea, N. Hirt-Burri, A. Jeannerat, L. A. Applegate, V. Ostafe, O. Jordan, G. Borchard, Peptide-decorated chitosan derivatives enhance fibroblast adhesion and proliferation in wound healing. Carbohydr. Polym. 142 (2016) 114-123. doi.org/10.1016/j.carbpol.2016.01.045.

[5] T.-C. Chou, Drug Combination Studies and Their Synergy Quantification Using the Chou-Talalay Method. Cancer Research 70 (2010) 440-446. 10.1158/0008-5472.can-09-1947.

[6] Tamis Darbre, Jean-Louis Reymond, Michaela Stach. (2015) Antimicrobial peptide dendrimers, Patent WO2015144928λ1.

[7] Timothy J. Falla, Lijuan Zhang, Scott M. Harris. (2007) Antimicrobial hexapeptides, Patent EP1853620λ2.

[8] C. D. Doern, When does 2 plus 2 equal 5?A review of antimicrobial synergy testing. Journal of clinical microbiology 52 (2014) 4124-4128. 10.1128/jcm.01121-14.

[9] A. Hennig, G. J. Gabriel, G. N. Tew, S. Matile, Stimuli-Responsive Polyguanidino-Oxanorbornene Membrane Transporters as Multicomponent Sensors in Complex Matrices. J. Am. Chem. Soc. 130 (2008) 10338-10344. doi.org/10.1021/ja802587j.

[10] S. M. Kelly, N. C. Price, The use of circular dichroism in the investigation of protein structure and function. Curr. Protein. Pept. Sci. 1 (2000) 349-384.

Burkatovskaya, M., Tegos, G. P., Swietlik, E., Demidova, T. N., A, P. C., & Hamblin, M. R. Use of chitosan bandage to prevent fatal infections developing from highly contaminated wounds in mice. Biomaterials, 2006; 27(22), 4157-4164.

Darbre T., Reymond J.-L., Stach M. Antimicrobial peptide dendrimers, 2014; EP 3 122 763 B1/WO-A1-2009/025691

Gan, B.-H., Siriwardena, T. N., Javor, S., Darbre, T., & Reymond, J.-L. Fluorescence Imaging of Bacterial Killing by Antimicrobial Peptide Dendrimer G$_3$KL. ACS Infectious Diseases, 2019; 5(12), 2164-2173.

Mishra B, Lushnikova T, Wang G. Small lipopeptides possess anti-biofilm capability comparable to daptomycin and vancomycin. RSC Adv. 2015; 5(73):59758-59769.

Sajomsang W, Tantayanon S, Tangpasuthadol V, Daly WH. Quaternization of N-aryl chitosan derivatives: synthesis, characterization, and antibacterial activity. Carbohydr Res. 2009; 344(18):2502-2511.

Sajomsang W, Gonil P, Saesoo S. Synthesis and antibacterial activity of methylated N-(4-N,N-dimethylaminocinnamyl) chitosan chloride. Eur Polym J. 2009; 45(8):2319-2328.

---

The invention claimed is:

1. A method for treating or decreasing the probability of developing a microbial infection in a patient in need thereof, the method comprising administering to the patient an active bio-conjugate comprising a chitosan derivative coupled to an antimicrobial peptide (AMP) according to the general formula (I):

C—S-L-Cys-AMP      (I)

wherein:
C is a chitosan derivative selected from the group consisting of O-carboxymethyl chitosan (CMC), O-carboxymethyl-N,N,N-trimethyl chitosan (TMC), N-(4-N, N-dimethylamino cinnamyl) chitosan (DMCMC), and methylated N-(4-pyridylmethyl) chitosan chloride (MPyMeC);
S is a spacer consisting of a $C_1$-$C_{12}$ aliphatic carbon chain terminated with one amino group at both ends;
L is a sulfo-crosslinker selected from the group consisting of: 4-(N-maleimidomethyl)cyclohexane-1-carboxylic acid 3-sulfo-N-hydroxysuccinimide (sulfo-SMCC); sulfosuccinimidyl 4-(N-maleimidophenyl)butyrate (sulfo-SMPB); sulfo-N-succinimidyl 4-maleimidobutyrate (sulfo-GMBS); N-(ε-maleimidocaproyloxy) sulfosuccinimide (sulfo-EMCS); N-(κ-maleimidoundecanoyloxy) sulfosuccinimide (sulfo-KMUS); sulfosuccinimidyl 6-[3'-(2-pyridyldithio)propionamido] hexanoate (sulfo-LC-SPDP), and sulfosuccinimidyl (4-iodoacetyl)aminobenzoate (sulfo-SIAB);
Cys is cysteine; and
AMP is a peptide or a peptide dendrimer, with the proviso that said peptide or peptide dendrimer is not a peptide consisting of arginine-glycine-aspartic acid (RGD); and
wherein said active bio-conjugate preserves its antimicrobial activity for at least 1 week when administered to the patient.

2. The method according to claim 1, wherein the AMP is a glycosylated or non-glycosylated linear peptide.

3. The method according to claim 2, wherein the linear peptide is selected from the group consisting of LinKL7, AG30, AG30/5C, AH90, CW49, Cys-KR12, hBD-1, His1, IDR-1018, KYKKALKKLAKLL (SEQ ID NO: 14), hL1-11, LL-37, Omiganan, OP-145, (cyclo)-RRRRRRR-(cyclo) (SEQ ID NO: 11), GIGKFLKKAKKFGKAFVKILKK (SEQ ID NO: 13), RH9L, Temporin A, Temporin B, and a combination thereof.

4. The method according to claim 1, wherein the AMP is a peptide dendrimer.

5. The method according to claim 1, wherein the microbial infection is selected from the group consisting of a bacterial, fungal, yeast, and viral infection.

6. The method according to claim 5, wherein the microbial infection is a bacterial infection.

7. The method according to claim 5, wherein the bacterial or yeast infection comprises a *Pseudomonas aeruginosa, Escherichia coli, S. aureus, S. epidermis, Klebsiellae pneumoniae, Acinetobacter baumannii, B. subtilis, E. aerogenes, C. freundii, Staphylococcus* spp, *Streptococcus* spp, *Enterococcus* spp, *Proteus* spp, *Candida* spp, *Apophysomyces* spp, *Aspergillus, Mucor* spp., *Porphymonas gingivalis, Prevotella intermedia, Treponema denticola, Tannerella forsythensis*, or *Aggregatibacter actinomycetemcomitans* infection.

8. The method according to claim 1, wherein the sulfo-crosslinker is selected from the group consisting of sulfo-N-succinimidyl 4-maleimidobutyrate (sulfo-GMBS), and sulfosuccinimidyl (4-iodoacetyl)aminobenzoate (sulfo-SIAB).

9. The method according to claim 1, wherein S is 1,12-diamino-alkane or 1,6-diamino-hexane.

10. The method according to claim 1, wherein a molar ratio between the chitosan derivative and the AMPs is 1-10/1-10.

11. The method according to claim 1, wherein the bioconjugate is present as a nanoparticle formulation.

12. The method according to claim 1, wherein the bioconjugate is present as a gel/hydrogel or a lyophilized foam formulation.

13. The method according to claim 12, wherein said formulation is for topical application.

14. The method according to claim 1, wherein the microbial infection comprises a bacterial infection disease, local bacterial infection, infected wound, abscess, soft tissue infection, diabetic infection, diabetic foot ulcer infection (DFU), osteomyelitis, burn infection, post-surgical wound infection, biomaterial-associated infection, or implant surface-associated infection.

15. The method according to claim 1, wherein the bioconjugate is administered as a pharmaceutical composition comprising a pharmaceutically acceptable carrier.

16. The method according to claim 4, wherein the peptide dendrimer selected from the group consisting of $G_1KL$, $G_2KL$, TNS18, $G_3KL$, $G_3RL$, $G_3KK_1$, $G_3KK_2$, $G_3LL_1$, $G_3LL_2$, $G_3KF$, $G_3KW$, $DG_3kl$, T4, T5, T7, T10, T13, T23, T25, T31, T32, T35, T36, and a combination thereof.

17. The method according to claim 6, wherein the bacterial infection is a gram-positive bacterial infection.

18. The method according to claim 6, wherein the bacterial infection is a gram-negative bacterial infection.

19. The method according to claim 5, wherein the microbial infection is a viral infection.

* * * * *

SEQUENCE LISTING

<160> NUMBER OF SEQ ID NOS: 19

<210> SEQ ID NO 1
<211> LENGTH: 30
<212> TYPE: PRT
<213> ORGANISM: Artificial Sequence
<220> FEATURE:
<223> OTHER INFORMATION: Anti microbial peptide

<400> SEQUENCE: 1

Met Leu Ser Leu Ile Phe Leu His Arg Leu Lys Ser Met Arg Lys Arg
1               5                   10                  15

Leu Asp Arg Lys Leu Arg Leu Trp His Arg Lys Asn Tyr Pro
            20                  25                  30

<210> SEQ ID NO 2
<211> LENGTH: 30
<212> TYPE: PRT
<213> ORGANISM: artificial
<220> FEATURE:
<223> OTHER INFORMATION: anti microbial peptide

<400> SEQUENCE: 2

Met Leu Lys Leu Ile Phe Leu His Arg Leu Lys Arg Met Arg Lys Arg
1               5                   10                  15

Leu Lys Arg Lys Leu Arg Leu Trp His Arg Lys Arg Tyr Lys
            20                  25                  30

<210> SEQ ID NO 3
<211> LENGTH: 24
<212> TYPE: PRT
<213> ORGANISM: artificial
<220> FEATURE:
<223> OTHER INFORMATION: anti microbial peptide

<400> SEQUENCE: 3

Ala Thr Ala Trp Asp Phe Gly Pro His Gly Leu Leu Pro Ile Arg Pro
1               5                   10                  15

Ile Arg Ile Arg Pro Leu Cys Gly
            20

<210> SEQ ID NO 4
<211> LENGTH: 11
<212> TYPE: PRT
<213> ORGANISM: artificial
<220> FEATURE:
<223> OTHER INFORMATION: anti microbial peptide

<400> SEQUENCE: 4

Ala Pro Phe Arg Met Gly Ile Cys Thr Thr Asn
1               5                   10

<210> SEQ ID NO 5

```
<211> LENGTH: 13
<212> TYPE: PRT
<213> ORGANISM: artificial
<220> FEATURE:
<223> OTHER INFORMATION: anti microbial peptide

<400> SEQUENCE: 5

Cys Lys Arg Ile Val Gln Arg Ile Lys Asp Phe Leu Arg
1               5                   10

<210> SEQ ID NO 6
<211> LENGTH: 36
<212> TYPE: PRT
<213> ORGANISM: Homo sapiens

<400> SEQUENCE: 6

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 7
<211> LENGTH: 38
<212> TYPE: PRT
<213> ORGANISM: homo sapiens

<400> SEQUENCE: 7

Asp Ser His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30

Asn Tyr Leu Tyr Asp Asn
        35

<210> SEQ ID NO 8
<211> LENGTH: 11
<212> TYPE: PRT
<213> ORGANISM: homo sapiens

<400> SEQUENCE: 8

Gly Arg Arg Arg Arg Ser Val Gln Trp Cys Ala
1               5                   10

<210> SEQ ID NO 9
<211> LENGTH: 12
<212> TYPE: PRT
<213> ORGANISM: artificial
<220> FEATURE:
<223> OTHER INFORMATION: AMP

<400> SEQUENCE: 9

Val Arg Leu Ile Val Ala Val Arg Ile Trp Arg Arg
1               5                   10

<210> SEQ ID NO 10
<211> LENGTH: 37
<212> TYPE: PRT
<213> ORGANISM: homo sapiens

<400> SEQUENCE: 10

Leu Leu Gly Asp Phe Phe Arg Lys Ser Lys Glu Lys Ile Gly Lys Glu
1               5                   10                  15
```

```
Phe Lys Arg Ile Val Gln Arg Ile Lys Asp Phe Leu Arg Asn Leu Val
            20                  25                  30

Pro Arg Thr Glu Ser
        35

<210> SEQ ID NO 11
<211> LENGTH: 7
<212> TYPE: PRT
<213> ORGANISM: artificial
<220> FEATURE:
<223> OTHER INFORMATION: AMP
<220> FEATURE:
<221> NAME/KEY: MISC_FEATURE
<222> LOCATION: (1)..(7)
<223> OTHER INFORMATION: cyclic formation

<400> SEQUENCE: 11

Arg Arg Arg Arg Arg Arg Arg
1               5

<210> SEQ ID NO 12
<211> LENGTH: 24
<212> TYPE: PRT
<213> ORGANISM: artificial
<220> FEATURE:
<223> OTHER INFORMATION: AMP

<400> SEQUENCE: 12

Ile Gly Lys Glu Phe Lys Arg Ile Val Glu Arg Ile Lys Arg Phe Leu
1               5                   10                  15

Arg Glu Leu Val Arg Pro Leu Arg
            20

<210> SEQ ID NO 13
<211> LENGTH: 22
<212> TYPE: PRT
<213> ORGANISM: artificial
<220> FEATURE:
<223> OTHER INFORMATION: AMP

<400> SEQUENCE: 13

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 14
<211> LENGTH: 13
<212> TYPE: PRT
<213> ORGANISM: artificial
<220> FEATURE:
<223> OTHER INFORMATION: AMP

<400> SEQUENCE: 14

Lys Tyr Lys Lys Ala Leu Lys Lys Leu Ala Lys Leu Leu
1               5                   10

<210> SEQ ID NO 15
<211> LENGTH: 13
<212> TYPE: PRT
<213> ORGANISM: Ranidea frog

<400> SEQUENCE: 15

Phe Leu Pro Leu Ile Gly Arg Val Leu Ser Gly Ile Leu
1               5                   10
```

```
<210> SEQ ID NO 16
<211> LENGTH: 13
<212> TYPE: PRT
<213> ORGANISM: artificial
<220> FEATURE:
<223> OTHER INFORMATION: AMP

<400> SEQUENCE: 16

Leu Leu Pro Ile Val Gly Asn Leu Leu Lys Ser Leu Leu
1               5                   10

<210> SEQ ID NO 17
<211> LENGTH: 14
<212> TYPE: PRT
<213> ORGANISM: artificial
<220> FEATURE:
<223> OTHER INFORMATION: AMPD

<400> SEQUENCE: 17

Lys Leu Lys Leu Lys Leu Lys Leu Lys Leu Lys Leu Lys Leu
1               5                   10

<210> SEQ ID NO 18
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 18

Arg Gly Asp Cys
1

<210> SEQ ID NO 19
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 19

Gly Arg Gly Asp Ser
1               5
```